(12) United States Patent
Cone et al.

(10) Patent No.: US 10,368,955 B2
(45) Date of Patent: Aug. 6, 2019

(54) MULTI-FUNCTIONAL FOOT PEDAL ASSEMBLY FOR CONTROLLING A ROBOTIC SURGICAL SYSTEM

(71) Applicant: Verb Surgical Inc., Mountain View, CA (US)

(72) Inventors: Taylor Joseph Cone, Palo Alto, CA (US); Joan Savall, Palo Alto, CA (US)

(73) Assignees: JOHNSON & JOHNSON INNOVATION-JJDC, INC., New Brunswick, NJ (US); VERILY LIFE SCIENCES LLC, South San Francisco, CA (US)

(*) Notice: Subject to any disclaimer, the term of this patent is extended or adjusted under 35 U.S.C. 154(b) by 96 days.

(21) Appl. No.: 15/476,454

(22) Filed: Mar. 31, 2017

(65) Prior Publication Data

US 2018/0280099 A1   Oct. 4, 2018

(51) Int. Cl.
| | |
|---|---|
| *A61B 34/00* | (2016.01) |
| *G05G 1/445* | (2008.04) |
| *B25J 13/04* | (2006.01) |
| *A61B 90/00* | (2016.01) |
| *A61B 34/37* | (2016.01) |
| *A61B 17/00* | (2006.01) |
| *H01H 3/14* | (2006.01) |
| *A61B 34/20* | (2016.01) |

(52) U.S. Cl.
CPC .............. *A61B 34/74* (2016.02); *B25J 13/04* (2013.01); *G05G 1/445* (2013.01); *A61B 34/37* (2016.02); *A61B 90/361* (2016.02); *A61B 2017/00477* (2013.01); *A61B 2017/00876* (2013.01); *A61B 2017/00973* (2013.01); *A61B 2034/2055* (2016.02); *A61B 2034/2059* (2016.02); *A61B 2090/061* (2016.02); *A61B 2090/067* (2016.02); *H01H 3/14* (2013.01)

(58) Field of Classification Search
USPC .................................................. 700/245–264
See application file for complete search history.

(56) References Cited

U.S. PATENT DOCUMENTS

| | | | |
|---|---|---|---|
| 4,965,417 A | 10/1990 | Massie | |
| 5,204,942 A * | 4/1993 | Otera ................. | G05B 19/4182 700/248 |
| 5,422,521 A | 6/1995 | Neer et al. | |
| 5,553,609 A * | 9/1996 | Chen .................. | G06F 19/3418 600/301 |
| 5,583,407 A | 12/1996 | Hiromitsu | |
| 5,635,777 A | 6/1997 | Telymonde et al. | |
| 5,704,791 A * | 1/1998 | Gillio ..................... | G09B 5/14 434/262 |
| 5,787,760 A | 8/1998 | Thorlakson | |

(Continued)

*Primary Examiner* — Jonathan L Sample
(74) *Attorney, Agent, or Firm* — Womble Bond Dickinson (US) LLP

(57) ABSTRACT

A foot pedal assembly for controlling a robotic surgical system includes a foot pedal assembly base including an axle, a foot pedal slidably and pivotally coupled to the axle, and a sensor arrangement configured to detect an axial position of the foot pedal along the axle and a pivoted position of the foot pedal around the axle. Different combinations of different detected axial positions and detected pivoted positions are correlateable to different functions of the robotic surgical system.

26 Claims, 17 Drawing Sheets

(56) References Cited

U.S. PATENT DOCUMENTS

| | | | | |
|---|---|---|---|---|
| 5,855,553 A * | 1/1999 | Tajima | A61B 34/70 | 600/407 |
| 5,876,325 A * | 3/1999 | Mizuno | A61B 1/00048 | 600/102 |
| 5,931,832 A * | 8/1999 | Jensen | B25J 9/1065 | 128/898 |
| 6,179,829 B1 * | 1/2001 | Bisch | A61C 1/0023 | 200/51.02 |
| 6,646,541 B1 * | 11/2003 | Wang | A61B 17/00 | 340/3.54 |
| 6,659,939 B2 * | 12/2003 | Moll | A61B 34/30 | 600/102 |
| 6,852,107 B2 * | 2/2005 | Wang | G05B 15/02 | 606/1 |
| 6,892,112 B2 * | 5/2005 | Wang | A61B 34/70 | 340/7.35 |
| 6,951,535 B2 * | 10/2005 | Ghodoussi | G06F 19/3418 | 600/101 |
| 7,245,202 B2 * | 7/2007 | Levin | H04L 12/282 | 307/114 |
| 7,865,266 B2 * | 1/2011 | Moll | A61B 34/30 | 700/245 |
| 7,877,171 B2 | 1/2011 | Gassner | | |
| 7,977,171 B2 | 1/2011 | Yang et al. | | |
| 8,340,863 B2 | 12/2012 | Karatsindes | | |
| 8,527,094 B2 * | 9/2013 | Kumar | G09B 23/28 | 700/259 |
| 8,914,150 B2 * | 12/2014 | Moll | A61B 34/30 | 700/246 |
| 9,039,681 B2 * | 5/2015 | Wang | G05B 15/02 | 606/1 |
| 9,119,654 B2 * | 9/2015 | Ramans | A61B 34/71 | |
| 9,301,811 B2 | 4/2016 | Goldberg et al. | | |
| 9,333,042 B2 * | 5/2016 | Diolaiti | A61B 90/37 | |
| 9,375,288 B2 | 6/2016 | Robinson et al. | | |
| 9,439,806 B2 | 9/2016 | Eastman et al. | | |
| 9,666,101 B2 * | 5/2017 | Kumar | G09B 23/28 | |
| 2002/0029095 A1 * | 3/2002 | Kosaka | B25J 9/1674 | 700/245 |
| 2003/0013949 A1 * | 1/2003 | Moll | A61B 34/30 | 600/407 |
| 2003/0047434 A1 * | 3/2003 | Hanson | A61B 17/00 | 200/86.5 |
| 2003/0050733 A1 * | 3/2003 | Wang | A61B 34/70 | 700/245 |
| 2003/0060927 A1 * | 3/2003 | Gerbi | G16H 40/63 | 700/245 |
| 2006/0166681 A1 * | 7/2006 | Lohbihler | G01S 5/02 | 455/456.2 |
| 2006/0178559 A1 * | 8/2006 | Kumar | A61B 34/37 | 600/109 |
| 2009/0036902 A1 * | 2/2009 | DiMaio | A61B 34/10 | 606/130 |
| 2011/0098721 A1 * | 4/2011 | Tran | H01H 21/26 | 606/130 |
| 2012/0029694 A1 * | 2/2012 | Muller | A61B 6/0407 | 700/248 |
| 2012/0283745 A1 * | 11/2012 | Goldberg | A61B 34/30 | 606/130 |
| 2013/0023899 A1 * | 1/2013 | Green | H04N 13/398 | 606/130 |
| 2013/0245834 A1 | 9/2013 | Laxhuber et al. | | |
| 2013/0331859 A1 * | 12/2013 | Kumar | A61B 34/37 | 606/130 |
| 2014/0195048 A1 * | 7/2014 | Moll | A61B 34/30 | 700/247 |
| 2014/0328469 A1 | 11/2014 | Lee et al. | | |
| 2014/0364864 A1 * | 12/2014 | Lynn | A61F 9/00745 | 606/107 |
| 2014/0378986 A1 * | 12/2014 | Eastman | A61B 17/00 | 606/107 |
| 2015/0029047 A1 | 1/2015 | Levasseur et al. | | |
| 2015/0003898 A1 | 2/2015 | Shiozaki | | |
| 2015/0038981 A1 | 2/2015 | Kilroy et al. | | |
| 2015/0051607 A1 * | 2/2015 | Hajishah | A61B 17/00 | 606/107 |
| 2018/0083621 A1 * | 3/2018 | Ekvall | H03K 17/975 | |
| 2018/0132948 A1 * | 5/2018 | Mercado | A61B 34/25 | |
| 2018/0280099 A1 | 10/2018 | Cone et al. | | |

* cited by examiner

MULTI-FUNCTIONAL FOOT PEDAL ASSEMBLY FOR CONTROLLING A ROBOTIC SURGICAL SYSTEM

TECHNICAL FIELD

This invention relates generally to the field of robotic surgery, and more specifically to new and useful systems and methods for controlling robotic surgical systems with a foot-operated system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical instruments (e.g., an end effector, at least one camera, etc.) through the incisions into the patient. The surgical procedures may then be performed using the introduced surgical instruments, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator. A robotic arm may, for example, support at its distal end various devices such as surgical end effectors, imaging devices, cannulae for providing access to the patient's body cavity and organs, etc.

To control conventional robotic surgical systems, a user at a user console may manipulate devices with hands and/or feet. For example, a typical user console may include foot pedals or buttons, where each foot pedal or button corresponds to a different respective function of the robotic surgical system. By moving his or her feet to manipulate different foot pedals or button, the user can control different functions of the system. For example, a particular foot pedal or buttons may correspond to actuation of a surgical instrument coupled to a particular robotic arm, or engagement or disengagement of a clutch mode, etc. Typically, each foot of the user must move among an array of multiple foot pedals or buttons to selectively control the various desired functions of the robotic surgical system. However, the user may accidentally select and engage the wrong foot pedal or button with their foot, thereby inadvertently actuating an undesired function of the robotic surgical system. For example, the user might not look down at their feet to visually locate the correct foot pedal or button. Additionally, even if the user does look down at their feet to ensure accurate foot placement on a desired foot pedal or button, such visual checking interrupts and slows the user's workflow. Although some systems may include a screen displaying to the user a graphical representation of their feet relative to foot pedal or buttons (e.g., based on sensor detection), visual checking of the screen to verify correct foot placement relies on accuracy of potentially erroneous sensor detection of foot placement, and additionally still interrupts and slows the user's workflow.

Therefore, it is desirable to have new and useful foot-operated control systems and methods for controlling a robotic surgical system.

SUMMARY

Generally, in some variations, a foot pedal assembly for controlling a robotic surgical system includes a foot pedal assembly base including an axle, a foot pedal slidably and pivotally coupled to the axle, and a sensor arrangement configured to detect an axial position of the foot pedal along the axle and a pivoted position of the foot pedal around the axle. The foot pedal assembly may be self-contained. For example, a self-contained foot pedal assembly is one that is complete and has all the components it needs to operate (translate, pivot, etc.) within the foot pedal assembly itself. It may be attached to a separate and additional mounting platform, but the actual limitations of movement of the foot pedal are defined by the foot pedal assembly and not the foot pedal's connection to a secondary mounting platform. Multiple foot pedal assemblies may be included in a user console for the robotic surgical system (e.g., two foot pedal assemblies, including one designated for a user's left foot and one designated for a user's right foot), such as mounted to a secondary mounting platform.

Different combinations of detected axial positions and detected pivoted positions may be correlateable to different functions of the robotic surgical system. For example, the detected axial position may be correlateable to a user-selected surgical instrument in the robotic surgical system, and/or the detected pivoted position may be correlateable to control of a function of a user-selected surgical instrument.

The foot pedal may have multiple axial positions along the axle and multiple pivoted positions around the axle that are correlateable to a particular function or are otherwise meaningful to a control system for the robotic surgical system. In some variations, the foot pedal may be biased (e.g., with springs or other biasing elements) to one or more axial positions and/or one or more pivoted positions. For example, the foot pedal may be bi-stable between two axial positions (e.g., the foot pedal may be urged toward one of the two axial positions, such as with one or more biasing elements). In another example, the foot pedal may additionally or alternatively be positionable at a third axial position, and the foot pedal assembly may further include at least one biasing element urging the foot pedal toward the third axial position. In some variations, the foot pedal assembly may include at least one biasing element urging the foot pedal to at least one pivoted position (e.g., a third pivoted position between two spaced-apart pivoted positions).

In some variations, the foot pedal may further include an intermediate component interposed between the foot pedal assembly base and the foot pedal. The intermediate component may be pivotally coupled to the axle such that the foot pedal and intermediate component may pivot around the axle in tandem. Additionally, the intermediate component may be substantially prevented from moving axially relative to the foot pedal assembly base, and the foot pedal may be laterally or translationally movable relative to the intermediate component. For example, the foot pedal may be configured to pivot with the intermediate component but move axially independently from the intermediate component.

In some variations, the foot pedal may be coupled to the axle such that the axle is farther from a first end of the foot pedal (e.g., a front portion of the foot pedal, from the perspective of a user operating the foot pedal) than a second end of the foot pedal (e.g., a rear portion of the foot pedal) opposite the first end. The foot pedal may have a positional reference, such as an arch bump on a surface engaging the user's foot, that helps locate the user's foot relative to the axle for improved ergonomics and pedal functionality, etc.

Generally, in some variations, a method for controlling a robotic surgical system includes detecting a translated position of a foot pedal relative to a foot pedal assembly base, detecting a pivoted position of the foot pedal relative to the foot pedal assembly base, and controlling the robotic surgical system in response to a combination of the detected translated position and the detected pivoted position of the foot pedal. The foot pedal assembly may be self-contained.

In some variations, the method may be used in combination with a system including a foot pedal that is translatable between a first translated position and a second translated position, and pivotable between a first pivoted position and a second pivoted position. While the foot pedal is detected to be in the first translated position, controlling the robotic surgical system may include controlling a first function of a first surgical instrument in response to detecting that the foot pedal is in the first pivoted position, and controlling a second function of the first surgical instrument in response to detecting that the foot pedal is in the second pivoted position. While the foot pedal is detected to be in the second translated position, controlling the robotic surgical system may include controlling a first function of a second surgical instrument in response to detecting that the foot pedal is in the first pivoted position, and controlling a second function of a second surgical instrument in response to detecting that the foot pedal is in the second pivoted position. Furthermore, when used in combination with a system including a foot pedal that is translatable to a third translated position (e.g., between the first and second translated positions), the method may include inhibiting control of one or more functions of a surgical instrument in response to detecting that the foot pedal is in the third translated position.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Robotic Surgical System Overview

Figure 1A:
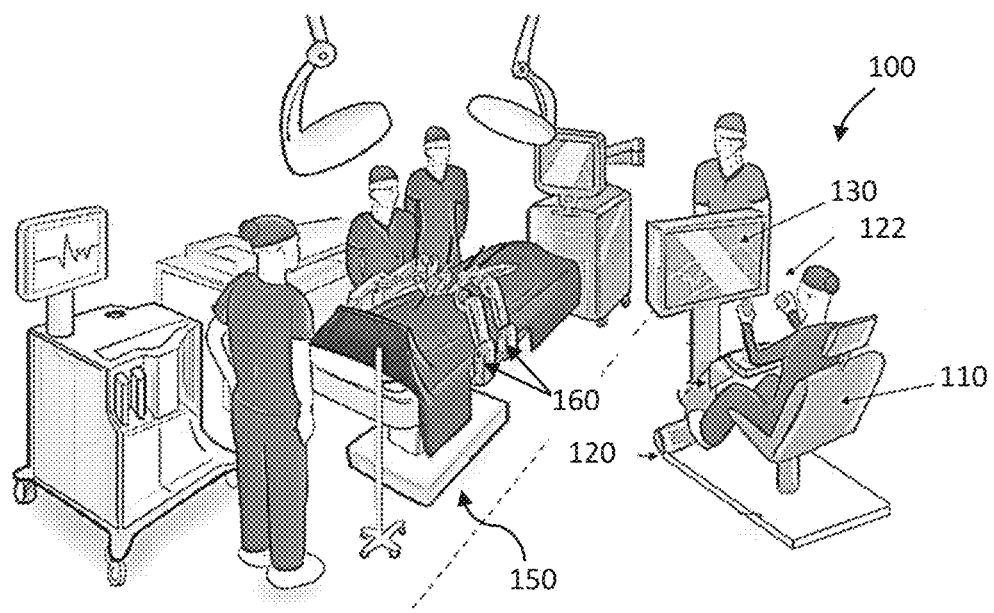
FIG. 1A depicts an example of an operating room arrangement with a robotic surgical system and a surgeon console.
Figure 1B:
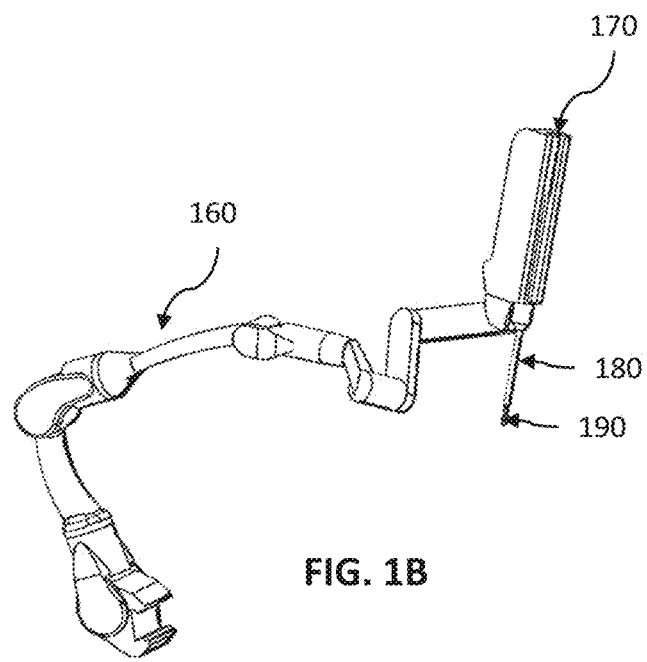
FIG. 1B is a schematic illustration of one exemplary variation of a robotic arm manipulator, tool driver, and cannula with a surgical tool.

Generally, as shown in FIG. 1A, a user console 100 may be part of a robotic surgical system for interfacing with a robotic system 150. The robotic system 150 may include one or more robotic arms 160 located at a surgical platform (e.g., table, bed, etc.), where end effectors or surgical tools are attached to the distal ends of the robotic arms 160 for executing a surgical procedure. For example, a robotic system 150 may include, as shown in the exemplary schematic of FIG. 1B, at least one robotic arm 160 coupled to a surgical platform, and a tool driver 170 generally attached to a distal end of the robotic arm 160. A cannula 100 coupled to the end of the tool driver 170 may receive and guide a surgical instrument 190 (e.g., end effector, camera, etc.). Furthermore, the robotic arm 160 may include a plurality of links that are actuated so as to position and orient the tool driver 170, which actuates the surgical instrument 190.

A user (such as a surgeon or other operator) may use the user console 100 to remotely manipulate the robotic arms 160 and/or surgical instruments (e.g., tele-operation). The user console 100 may be located in the same procedure room as the robotic system 150, as shown in FIG. 1A. In other embodiments, the user console 100 may be located in an adjacent or nearby room, or tele-operated from a remote location in a different building, city, or country.

Figure 1C:
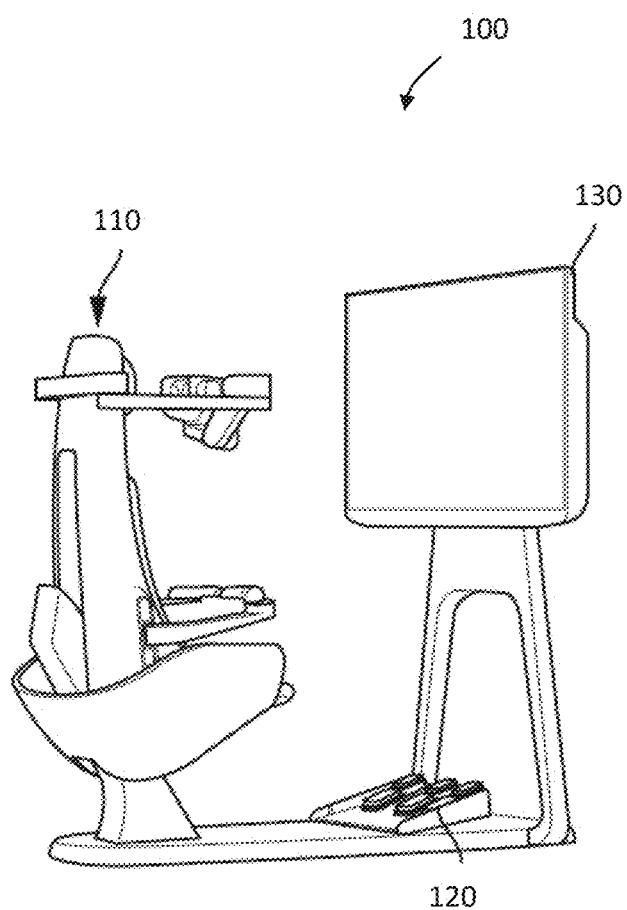
FIG. 1C is a schematic illustration of an exemplary surgeon console.

In one example, the user console 100 comprises a seat 110, foot-operated controls 120, one or more handheld user interface devices 122, and at least one user display 130 configured to display, for example, a view of the surgical site inside a patient. For example, as shown in the exemplary user console shown in FIG. 1C, a user located in the seat 110 and viewing the user display 130 may manipulate the foot-operated controls 120 and/or handheld user interface devices to remotely control the robotic arms 160 and/or surgical instruments. The foot-operated controls 120 and/or handheld user interface devices may additionally or alternatively be used to control other aspects of the user console 100 or robotic system 150. For example, in variations in which the user generally controls (at any given time) a designated "left-hand" robotic arm/instrument and a designated "right-hand" robotic arm/instrument, the foot-operated controls 120 may enable a user to designate from among a larger group of available robotic arms/instruments which robotic arms/instruments comprise the "left-hand"

and "right-hand" robotic arm/instruments (e.g., via toggle or rotation in selection among the available robotic arms/instruments). Other examples include adjusting or configuring the seat 110, the foot-operated controls 120, the user interface devices 122, and/or the user display 130. Further exemplary variations of the foot-operated controls 120 are described herein.

During an exemplary procedure or surgery, the patient is prepped and draped in a sterile fashion, and anesthesia is achieved. Initial access to the surgical site may be performed manually with the robotic system 150 in a stowed configuration or withdrawn configuration to facilitate access to the surgical site. Once access is completed, initial positioning and/or preparation of the robotic system may be performed. During the surgical procedure, a surgeon or other user in the user console 100 may utilize the foot-operated controls 120 and/or user interface devices 122 to manipulate various end effectors and/or imaging systems to perform the procedure. Manual assistance may also be provided at the procedure table by sterile-gowned personnel, who may perform tasks including but not limited to retracting organs, or performing manual repositioning or tool exchange involving one or more robotic arms 160. Non-sterile personnel may also be present to assist the surgeon at the user console 100. When the procedure or surgery is completed, the robotic system 150 and/or user console 100 may be configured or set in a state to facilitate one or more post-operative procedures, including but not limited to robotic system 150 cleaning and/or sterilization, and/or healthcare record entry or printout, whether electronic or hard copy, such as via the user console 100.

In FIG. 1A, the robotic arms 160 are shown with a table-mounted system, but in other embodiments, the robotic arms may be mounted in a cart, ceiling or sidewall, or other suitable support surface. The communication between the robotic system 150, the user console 100, and any other displays may be via wired and/or wireless connection(s). Any wired connections may be optionally built into the floor and/or walls or ceiling. The communication between the user console 100 and the robotic system 150 may be wired and/or wireless, and may be proprietary and/or performed using any of a variety of data communication protocols. In still other variations, the user console 100 does not include an integrated display 130, but may provide a video output that can be connected to output to one or more generic displays, including remote displays accessible via the internet or network. The video output or feed may also be encrypted to ensure privacy and all or portions of the video output may be saved to a server or electronic healthcare record system.

In other examples, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Foot Pedal Assembly

Figure 2A:
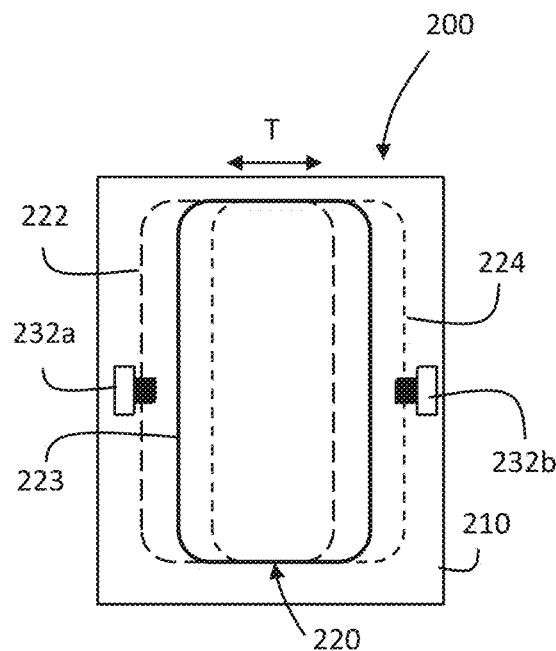
FIGS. 2A and 2B are top and side view schematic illustrations of one variation of a foot pedal assembly.
Figure 2B:
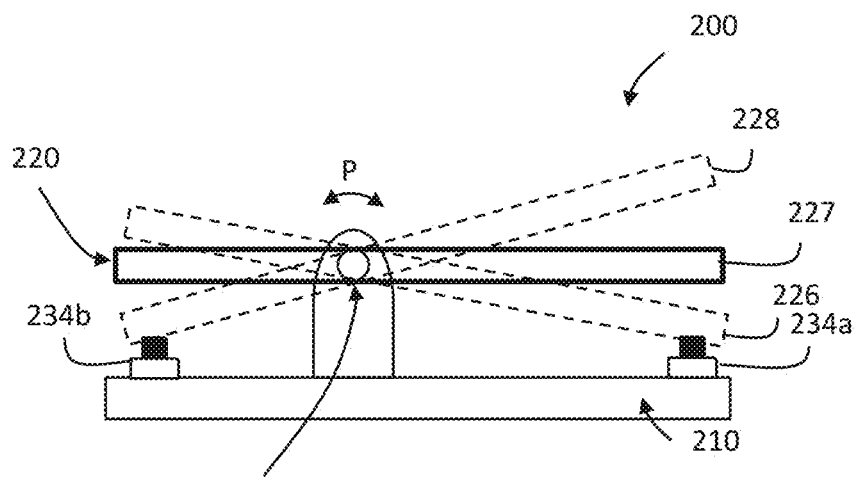
Figure 2C:
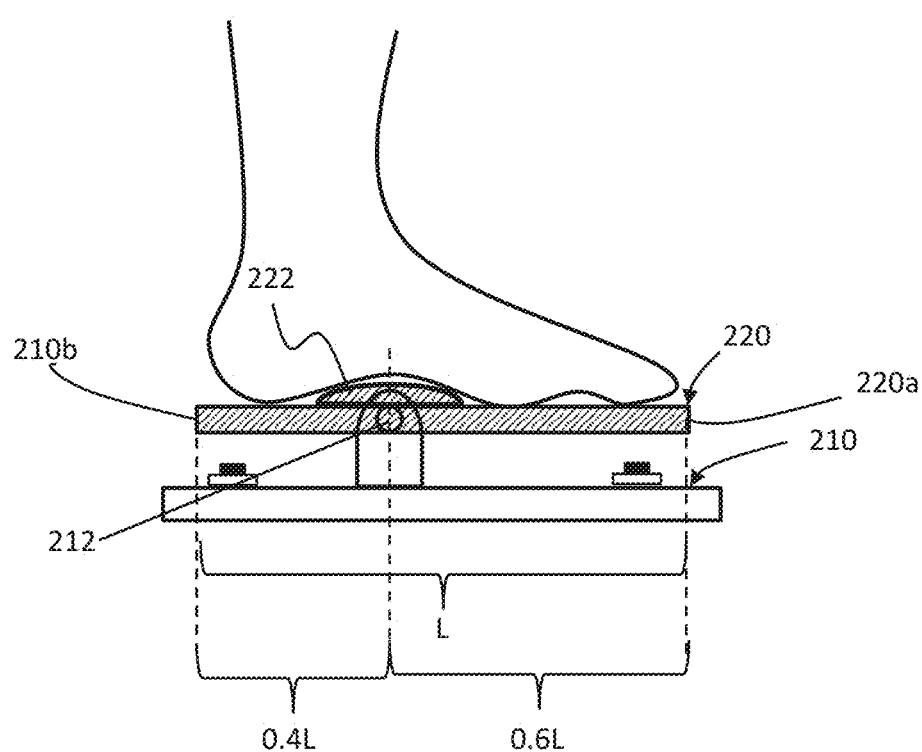
FIG. 2C is another side view schematic illustration of axle placement in one variation of foot pedal assembly.

FIGS. 2A-2C are illustrative schematics of general mechanics and other operations of a foot pedal assembly, exemplary variations of which are described in further detail herein. As shown in FIGS. 2A and 2B, a foot pedal assembly 200 for controlling a robotic surgical system includes a foot pedal assembly base 210, a foot pedal 220 translatable and pivotable relative to the foot pedal assembly base 210, and a sensor arrangement configured to detect a translated position and a pivoted position of the foot pedal 220. In some variations, the foot pedal assembly 200 may be self-contained. For example, a self-contained foot pedal assembly is one that is complete and has all the components it needs to operate (translate, pivot, etc.) within the foot pedal assembly itself. It may be attached to (or rest on) a separate and additional mounting platform, but the actual limitations of movement of the foot pedal are defined by the foot pedal assembly and not the foot pedal's connection to a secondary mounting platform. The foot pedal assembly 200 may be included in a user console for a robotic surgical system as described above, although it should be understood that in other variations the foot pedal assembly 200 may be used to control other suitable kinds of robotic systems.

Generally, different combinations of different detected translated positions and pivoted positions may be correlateable to control of different functions of the robotic surgical system, as further described herein. For example, in one variation, different translated positions of the foot pedal may generally correspond to control of different surgical instruments (e.g., instruments on different robotic arms), such that a user may, for example, move the foot pedal to a selected translated position to enable control of a selected surgical instrument. While the foot pedal is in the selected translated position, different pivoted positions of the foot pedal may generally correspond to actuation of different functions of the selected surgical instrument (e.g., a primary active function or a secondary active function of the surgical instrument). In other variations, different translated positions of the foot pedal need not correspond to different surgical instruments or robotic arms. For example, various combinations of translated positions and pivoted positions of the foot pedal relative to the foot pedal assembly base may correspond to any suitable assortment of distinct functions of the robotic surgical system (e.g., an instrument clutch mode, camera control, selection or designation of a "left hand" and "right hand" pair or other suitable subset of available robotic arms/instruments for control, etc.).

In conventional foot pedal controls for controlling robotic surgical systems, each foot pedal corresponds to a respective, single function (e.g., a primary active function of a designated "left hand" instrument, a secondary active function of a designated "left hand" instrument, etc.), which requires a user to navigate their foot to the correct pedal to control a particular desired functionality. Current foot pedal controls increase the risk of actuating an undesired functionality (e.g., if the user does not realize he or she has located and actuated the wrong pedal), and/or interrupt workflow by requiring the user to pause and confirm (e.g., visually) that they have located the correct pedal for the desired functionality.

In contrast, the foot pedal assembly 200 and its variations described herein may combine the functionalities of multiple pedals into a single pedal, thereby enabling foot-operated controls 120 to have fewer pedals without sacrificing range of functionality. For example, one exemplary variation of foot-operated controls may include two foot pedal assemblies 200, one to be operated by a left foot of a user and another to be operated by a right foot of a user. In this variation, each foot pedal assembly 200 may have two translated positions (e.g., a left position and a right position) and two pivoted positions (e.g., forward position and rearward position) that may, in combination, enable control of four separate functionalities corresponding to: (i) a "left" and "forward" combination, (ii) a "left" and "rearward" combination, (iii) a "right" and "forward" combination, and (iv) a "right" and "rearward" combination. A total of eight separate functionalities of a system may be controlled with two such foot pedal assemblies 200. Accordingly, a user using two feet to operate two such foot pedal assemblies 200 may control any of the eight functionalities corresponding to the foot pedal assemblies 200 without physically moving their feet to any other separate pedals, such that the foot pedal assemblies 200 may enable easier and more accurate control of many desired functionalities of the robotic system. Such control may also be more ergonomic, since the user need not strain to reach distant pedals. Additionally, a multi-functional foot pedal assembly 200 providing n functionalities (where n>1) is more compact than n separate pedals that each provides one respective functionality, and is more compact without sacrificing range of functionality. Although in some variations more than two foot pedal assemblies 200 may be included in a user console, such multi-functionality of each assembly 200 still provides advantages in risk reduction, ergonomics, and space-saving features, etc., discussed herein.

Figure 2D:
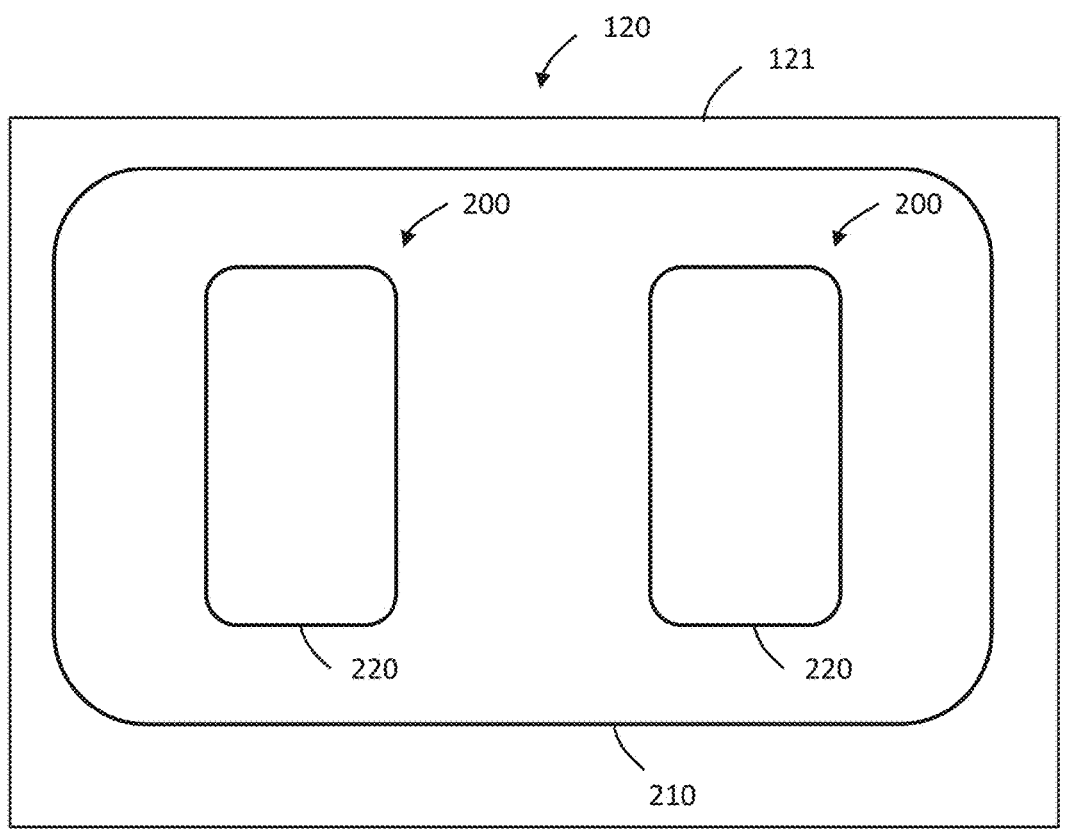
FIG. 2D is a top view schematic illustration of two foot pedal assemblies included in an exemplary user console.

One or more foot pedal assemblies 200 may be included in foot-operated controls 120 for a robotic system. The foot-operated controls 120 may, for example, be located near a user seat 110 in a user console 100 for a robotic surgical system as shown in FIG. 1A. As shown in FIG. 2D, foot-operated controls 120 in a user console may include multiple foot pedal assemblies 200, such as two foot pedal assemblies 200 (e.g., one for a user's left foot and one for a user's right foot), or another suitable number. In some variations, each of the multiple foot pedal assemblies 200 may have its own respective foot pedal assembly base 210. In other variations, multiple foot pedal assemblies 200 may share the same foot pedal assembly base 210 (e.g., two or more foot pedals 220 may move relative to the same common foot pedal assembly base 210). The foot pedal assembly base 210 may be coupled to (or rest on) a separate mounting platform (e.g., mounting platform 121).

The foot pedal assembly base 210 may generally include, for example, a platform or other suitable structure for supporting movement of the foot pedal 220 relative to the foot pedal assembly base 210. Other exemplary details of the foot pedal assembly base 210 are further described in variations described below.

The foot pedal 220 may be configured to engage with and be actuated by a user's foot to provide control input to the robotic surgical system. The foot pedal 220 may, in some variations, be longer along a longitudinal dimension than along a lateral dimension generally orthogonal to the longitudinal dimension (e.g., having an aspect ratio similar to a human foot which generally has a length greater than its width). For example, as shown in FIG. 2A, the foot pedal 220 may be generally rectangular. In other variations, the foot pedal 220 may be elliptical, square, circular, or have any suitable shape.

Generally, the foot pedal 220 may be actuated by a user throughout a translational range of motion and a pivotal range of motion relative to the foot pedal assembly base 210, where the translational range of motion and/or pivotal range of motion include one or more discrete "active" positions. An "active" position may be a position that activates or triggers a change in a functionality of the robotic system. For example, an "active" position may activate or turn on a particular functionality of the robotic system, suspend or turn off a particular functionality of the robotic system, modulate or modify a parameter (e.g., power, current, voltage, duty cycle, duration, speed, etc.) relating to a particular functionality of the robotic system, etc. In some variations, the translational range of motion and/or pivotal range of motion may additionally include one or more discrete functionally "neutral" positions (e.g., positioning at a "neutral" position does not activate or trigger a change in a functionality of the robotic system, may afford the user an opportunity to rest his or her foot with no intention to affect a change in the robotic system, etc.).

For example, as shown in FIG. 2A, a top view (e.g., from the perspective of a user looking down at the foot pedal assembly 200) of an exemplary foot pedal assembly 200 depicts a foot pedal 220 having a translational range of motion along the direction T (e.g., lateral motion, or left and right motion from the perspective of a user looking down at the foot pedal assembly base 210). The translational range of motion may include, for example, a first lateral position 222 (e.g., toward a left portion of the foot pedal assembly base 210) and a second lateral position 224 (e.g., toward a right portion of the foot pedal assembly base 210). In some variations, the first and/or second lateral positions 222 and 224 may be "active" positions, or alternatively may be "neutral" positions. Furthermore, in some variations, the translational range of motion may include a third lateral position 223 between the first and second lateral positions 222 and 224 (and/or any additional discrete lateral positions), where the third lateral position 223 may be an "active" position, or alternatively a "neutral" position. It should be understood that the foot pedal may additionally or alternatively be movable in other translated directions (e.g., forward and backward translation in a direction orthogonal to the direction T, etc.). Furthermore, the foot pedal may additionally or alternatively be movable in other lateral directions (e.g., lateral rotation generally within a lateral plane, lateral tilting generally left and right, etc.). Furthermore, the foot pedal assembly may include multiple operating modes, where a given translated or lateral position (e.g., first, second, or third position) may be "active" or "neutral" depending on the operating mode. As further described herein, different "active" translated or lateral positions of the foot pedal may, in combination with different pivotal positions of the foot pedal, be correlateable to different functions of the robotic surgical system.

As another example, as shown in FIG. 2B, a side view of the exemplary foot pedal assembly 200 depicts a foot pedal 220 having a pivotal range of motion around an axle 212 supported by the foot pedal assembly base 210, in the direction P. The pivotal range of motion may include, for example, a first pivoted position 226 (e.g., pivoted toward a forward portion of the foot pedal assembly base 210 from the perspective of a user facing toward the right side of FIG. 2B) and a second pivoted position 228 (e.g., pivoted toward a rearward portion of the foot pedal assembly base 210). In some variations, the first and second pivoted positions 226 and 228 may be "active" positions, or alternatively may be "neutral" positions. Furthermore, in some variations, the pivotal range of motion may include a third pivoted position 227 between the first and second pivoted positions 226 and 228, (and/or any additional discrete pivoted positions), where the third pivoted position 227 may be an "active" position, or alternatively a "neutral" position. Furthermore, the foot pedal assembly may include multiple operating modes, where a given pivoted position (e.g., first, second, or third pivoted position) may be "active" or "neutral" depending on the operating mode. As further described herein, different "active" pivoted positions may, in combination with different translated or lateral positions of the foot pedal, be correlateable to actuation of different functions of the robotic system. As further described herein, different "active" pivoted positions of the foot pedal may, in combination with different translated positions of the foot pedal, be correlateable to different functions of the robotic surgical system.

In some variations, as shown in FIG. 2C, the foot pedal 220 may be coupled to the axle 212 such that the axle 212 is located between a first end 220a and a second end 220b of the pedal, so as to enable the foot pedal 220 to pivot toward a first end of the foot pedal assembly base to achieve a first pivoted position, and further enable the foot pedal 220 to pivot toward a second end of the foot pedal assembly base to achieve a second pivoted position.

In some variations, the axle 212 may be longitudinally offset along the pedal, or located closer to one end of the pedal than the other end of the pedal. Generally, the weight of a user's leg may tend to result in unequal weight distribution across the user's foot, in that a user's leg weight is generally biased toward the heel of the user's foot than toward the forefront of the user's foot when the user is sitting or reclined in a seat. Such weight bias may, in some instances, increase the risk of an inadvertent rearward actuation of the foot pedal 220 (toward a rearward pivoted position corresponding to a particular function of the robotic surgical system) when the user is simply resting his or her foot on the foot pedal 220. By having including an axle 212 closer to the rear end of the pedal 220, the foot pedal assembly 200 may better support the weight of the user's leg, thereby offsetting the weight bias and reducing the likelihood of inadvertent rearward actuation of the foot pedal 220. Additionally, the location of the axle 212 may be selected to improve comfortable ergonomics for the user desiring to pivotably actuate the foot pedal 220. For example, generally, the more rearward the location of the axle 212 (e.g., closer to the second end 220b pictured in FIG. 2C), the greater an angle the user's foot must actuate the foot pedal 220 in order to achieve a fully forward pivoted position (e.g., to engage a switch at a front end of the foot pedal assembly base 210). Thus, in some variations, as shown in FIG. 7, the axle 212 may be positioned farther from the first end 220a and closer to the second end 220b of the pedal to mitigate user discomfort. In variations in which the first end 220a corresponds to a front end of the pedal and the second end 220b corresponds to a rear end of the pedal relative to a user's foot, the axle 212 may be longitudinally offset toward the rear end of the pedal. For example, the axle 212 may be located at a longitudinal location along the pedal 220 that is between about 30% and about 49% of the pedal's length from a rear pedal end (i.e., between about 70% and about 51% of the pedal's length from a front pedal end), or between about 35% and about 45% of the pedal's length from a rear pedal end (i.e., between about 65% and 55% of the pedal's length from a front pedal end). For example, as shown in FIG. 2C, for a pedal having length L, the axle 212 may be located about 0.4L distance from a rear pedal end and about 0.6L distance from a front pedal end (40% of the pedal's length from a rear pedal end and 60% of the pedal's length from a front pedal end).

In some variations, a surface of the foot pedal 220 may include a reference to the user indicating an optimized placement of his or her foot on the foot pedal relative to the axle. For example, as shown in FIG. 2C, the reference may include an arch bump 222 generally centered over the axle 212 and which may provide a tactile reference point for the user to position his or her foot on the foot pedal 220. Such an arch bump 222 may, for example, additionally provide ergonomic contouring to a user's foot. Other examples include footprint outlines (e.g., for different foot sizes) that are printed or embossed on the foot pedal, one or more movable end pieces (e.g., heel stops or toe stops) that are repositionable to physically constrain and locate different foot sizes relative to the axle 212, etc. Furthermore, in some variations, a surface of the foot pedal 220 may include textural or frictional features (e.g., ribbings, bumps, frictional material, etc.) and/or fasteners (e.g., straps, laces, toe clips, etc.) to help the user's foot securely engage with the foot pedal 220 and reduce slipping.

The sensor arrangement may include one or more sensors configured to detect a translated position and a pivoted position of the foot pedal 220 relative to the foot pedal assembly base 210, for example as the user actuates the foot pedal 220 in translation and/or pivoting. In some variations, the sensor arrangement may include one or more switches (e.g., button switches, slide switches, toggle switches, etc.). For example, as shown in FIG. 2A, an exemplary sensor arrangement includes a first switch 232a and a second switch 232b coupled to the foot pedal assembly base. When the foot pedal 220 is in the first lateral position 222, the foot pedal 220 engages the first switch 232a, thereby causing the first switch 232a to provide a signal to a control system (not shown) indicating detection of the foot pedal 220 in the first lateral position 222. Similarly, when the foot pedal 220 is in the second lateral position 224, the foot pedal 220 engages the second switch 232b, thereby causing the second switch 232b to provide a signal to the control system indicating detection of the foot pedal 220 in the second lateral position 224. Furthermore, as shown in FIG. 2B, an exemplary sensor arrangement may include a third switch 234a and a fourth switch 234b coupled to the foot pedal assembly base 210. When the foot pedal 220 is in the first pivoted position 226, the foot pedal engages the third switch 234a, thereby causing the third switch 234a to provide a signal to the control system indicating detection of the foot pedal 220 in the first pivoted position 226. Similarly, when the foot pedal 220 is in the second pivoted position 228, the foot pedal engages the fourth switch 234b to provide a signal to the control system indicating detection of the foot pedal 220 in the second pivoted position 228. Additional switches or other sensors may be provided to detect when the foot pedal 220 is in other translated and/or pivoted positions.

Although FIGS. 2A and 2B illustrate a sensor arrangement including switches, other variations of the sensor arrangement may additionally or alternatively include other kinds of sensors. For example, proximity sensors (e.g., infrared sensor) or contact sensors (e.g., capacitive, inductive) may be positioned on the foot pedal assembly base 210 and/or foot pedal 220 to detect when the foot pedal 220 has approached or contacted the area of the foot pedal assembly base 210 corresponding to an "active" lateral or pivoted position of the foot pedal (e.g., the first or second lateral positions of the foot pedal, or the first or second pivoted positions of the foot pedal). As another example, one or more markers (e.g., infrared markers) may be coupled to the foot pedal 220 to facilitate optical tracking of the lateral and/or pivoted position of the foot pedal 220 via one or more overhead tracking sensors and/or sensors surrounding the foot pedal 220 to detect lateral positioning and/or pivoted positioning of the foot pedal. As yet another example, the sensor arrangement may include at least one analog or continuous sensor (e.g., potentiometer, encoder, capacitive sensor, etc.) for detecting the lateral and/or pivoted position of the foot pedal within at least a portion of the foot pedal's range of motion. Furthermore, the sensor arrangement may include at least one single degree of freedom sensor (detecting position only in one of the foot pedal's degrees of freedom, such as only lateral movements or only pivoted movements), or may additionally or alternatively include at least one multiple degree of freedom sensor (detecting position in two or more of the foot pedal's degrees of freedom). Other variations may include any suitable discrete and/or continuous (and single-degree of freedom or multi-degree of freedom) sensors for detecting position of the foot pedal. In some variations, the foot pedal assembly may include one or more switches in combination with one or more proximity sensors and/or markers for optical tracking, and/or any other suitable sensors. Signals from the sensor arrangement may be used, as further described herein, to control different functions of the robotic system.

Figure 3:
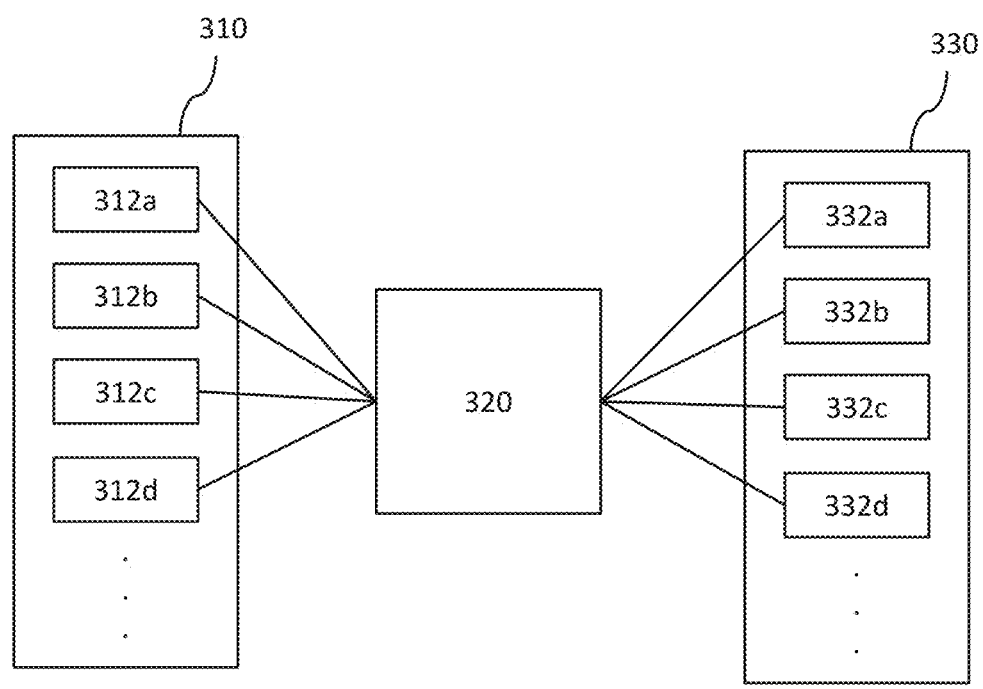
FIG. 3 is a connection diagram schematically depicting exemplary communication between a foot pedal assembly, a processor/controller, and a robotic surgical system.

As shown in the schematic of FIG. 3, sensor signals from one or more foot pedal assemblies 310 may be communicated to a processor/controller 320. For example, signals from one or more sensors (312a, 312b, 312c, 312d, etc.) may indicate translated position and/or pivoted position of the foot pedal in a foot pedal assembly 310. These sensor signals may be communicated (e.g., via a wired or wireless connection) to the processor/controller 320. The processor/controller 320 may generate and communicate control signals (e.g., electrical signals) to control portions of the robotic surgical system 330. For example, the processor/controller 330 may generate and communicate control signals to control actuation of a user-selected function of a user-selected surgical instrument (e.g., fire an energy pulse, actuate graspers, actuate cutters, control a camera, or activate any suitable surgical instrument 332a, 332b, 332c, 332d, etc.), engage an instrument clutch mode (e.g., movement of handheld user interface devices does not move surgical instruments otherwise controlled by the user interface devices), select or designate a subset of available robotic arms/instruments for present control, etc. Furthermore, the sensors in the sensor arrangement may be configured to detect translated and/or pivoted positions of the foot pedal 220 relative to the foot pedal assembly base throughout its translating and/or pivoting ranges of motion. Sensor signals indicating current placement of the foot pedal may be communicated to a processor/controller 320 and used to display a graphical representation on a display of the current foot pedal position, such as to inform the user of current position for spatial awareness of the foot pedal, imminent actuation of the foot pedal to an "active" translated or pivoted position, etc.

Figure 4A:
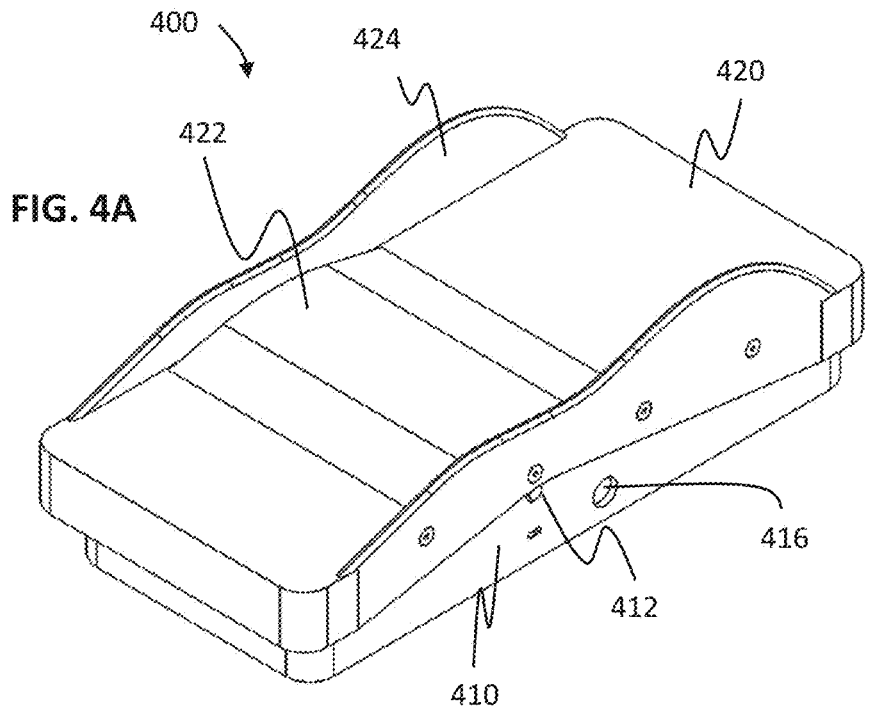
FIG. 4A is a perspective view of one variation of a foot pedal assembly.
Figure 4B:
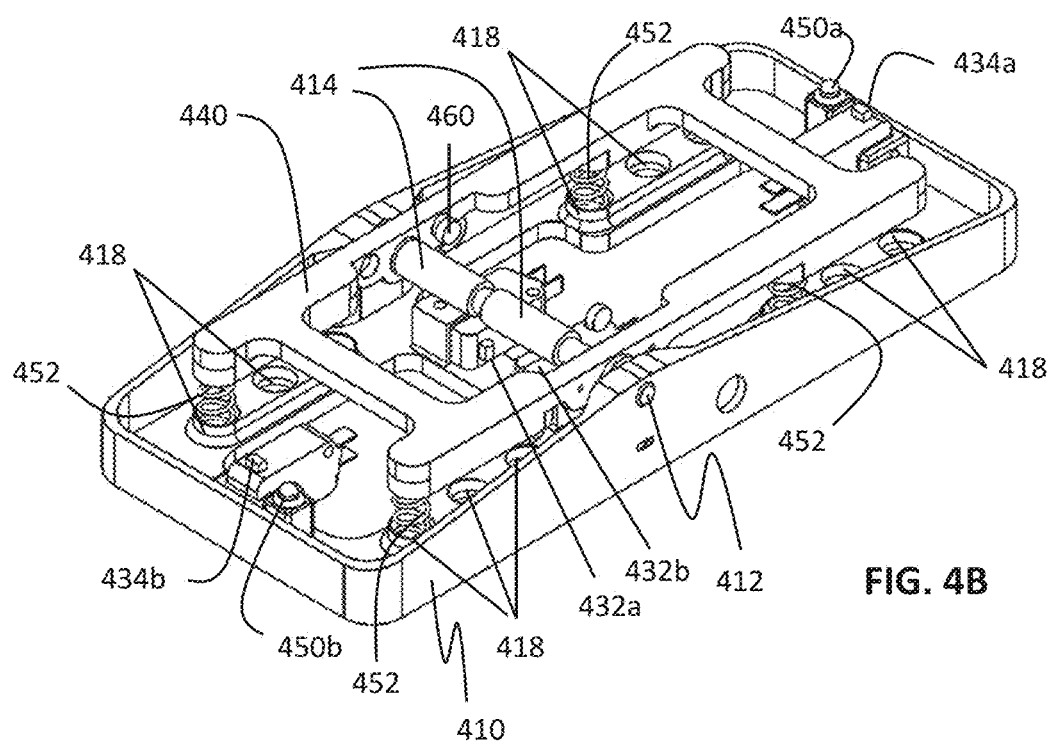
FIG. 4B is a partial perspective view of the foot pedal assembly shown in FIG. 4A, omitting at least the foot pedal.

One exemplary variation of a foot pedal assembly is shown in FIGS. 4A-4F. As shown in FIGS. 4A and 4B, a foot pedal assembly 400 for controlling a robotic surgical system may include a foot pedal assembly base 410 including an axle 412, a foot pedal 420 slidably and pivotally coupled to the axle 412, and a sensor arrangement including one or more sensors configured to detect an axial position of the foot pedal 420 along the axle 412 and a pivoted position of the foot pedal 420 around the axle 412. The foot pedal assembly 400 may include an intermediate component 440 located between the foot pedal assembly base 410 and the foot pedal 420, where the intermediate component 440 helps isolate the mechanics of the foot pedal in its axial movement from the mechanics of the foot pedal in its pivotal movement (e.g., helps prevent axial movement of the foot pedal along the axle from interfering with pivotal movement, as described further below). Furthermore, in some variations, the foot pedal assembly 400 may be self-contained. For example, a self-contained foot pedal assembly is one that is complete and has all the components it needs to operate (translate, pivot, etc.) within the foot pedal assembly itself. It may be attached to (or rest on) a separate and additional mounting platform, but the actual limitations of movement of the foot pedal are defined by the foot pedal assembly and not the foot pedal's connection to a secondary mounting platform.

The foot pedal assembly base 410 may provide structural support for the foot pedal 420, intermediate component 440, and/or other components of the foot pedal assembly 400, such as springs or sensors described in further detail below. Furthermore, the foot pedal assembly base 410 may facilitate mounting of the foot pedal assembly 410 to a grounding surface (e.g., a surface in a user console or a ground of a room), such that, for example, the foot pedal assembly base 410 may be kept substantially stationary as the foot pedal 420 moves. The foot pedal assembly base 410 may, for example, couple to a separate mounting platform or other suitable coupling surface of the user console via fasteners (e.g., screws, bolts, adhesive, hook-and-loop fasteners, etc.). In other examples, the foot pedal assembly base 410 may couple to a surface through physical interference (e.g., a bottom projection of the foot pedal assembly base 410 mating with a recess in a pedal tray or other surface, or vice versa). In yet other examples, the foot pedal assembly base 410 may include (e.g., on an underside surface of the foot pedal assembly base 410) textural features such as bumps, grip tape, etc. that may frictionally engage with a grounding surface.

The foot pedal assembly base 410 may, in some variations, be longer in a longitudinal direction than along a lateral direction generally orthogonal to the longitudinal dimension (e.g., so as to accommodate a foot pedal having an aspect ratio similar to a human foot which generally has a length greater than its width). For example, as shown in FIG. 4B, the foot pedal assembly base 410 may be generally rectangular, being longer in one dimension than in another dimension. In other variations, the foot pedal assembly base 410 may be elliptical, or have any suitable general shape.

As shown in FIG. 4B, the foot pedal assembly base 410 may include a housing with one or more raised walls. The foot pedal assembly base 410 may, for example, house at least the intermediate component 440, one or more springs 452 supporting the foot pedal 420 throughout its motions and/or one or more sensors for detecting axial or pivoted positions of the foot pedal. Furthermore, in some variations, the foot pedal assembly base 410 may include routing for sensor communication, such as a cable port opening 416 in a housing wall that allows passage of sensor cables (for carrying signals, powers, etc.) in and out of the housing.

Figure 4C:
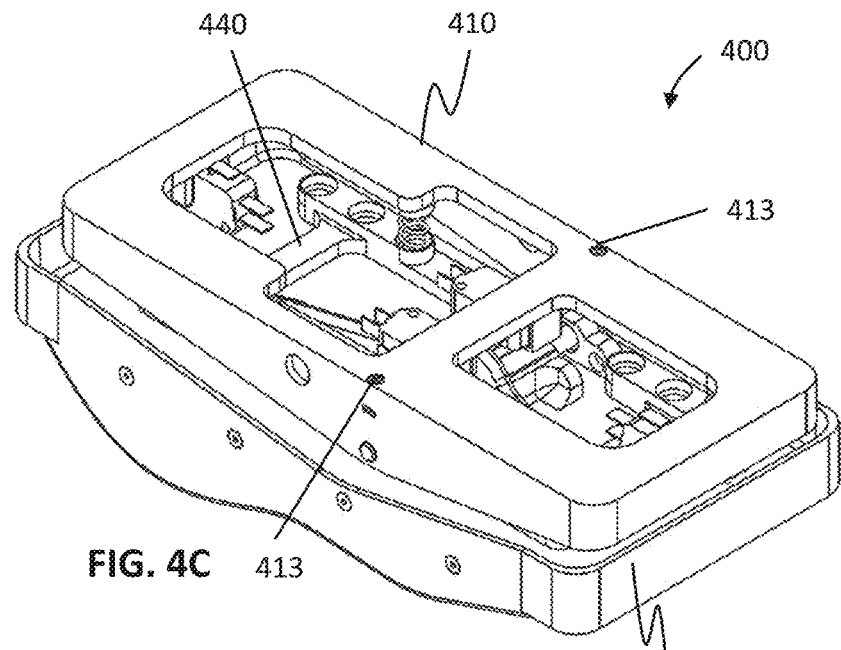
FIG. 4C is a bottom perspective view of the foot pedal assembly shown in FIG. 4A.
Figure 4D:
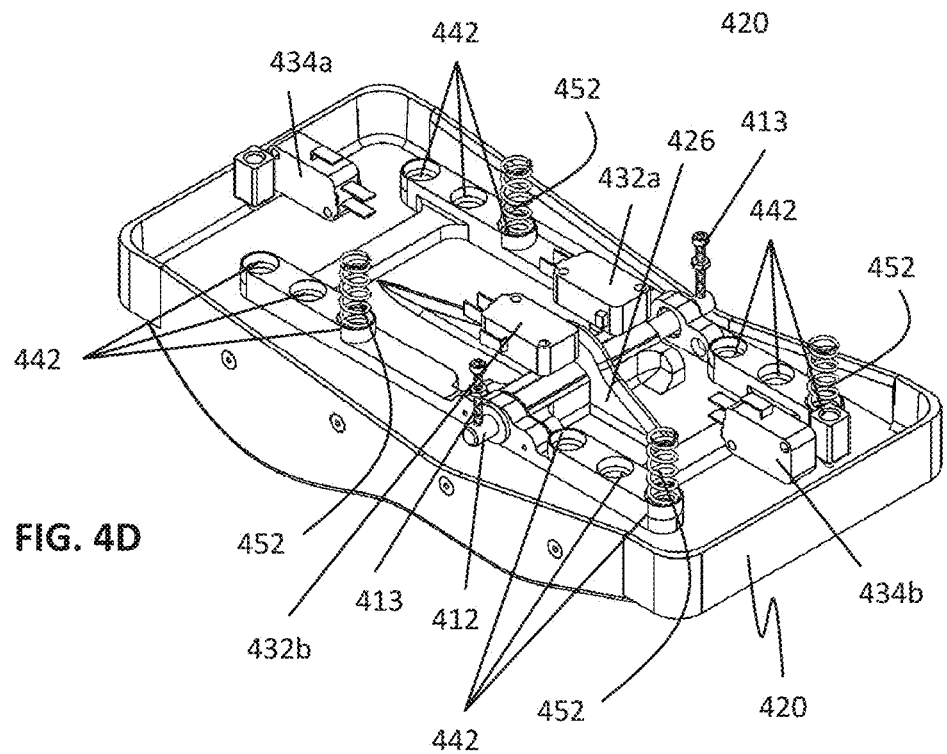
FIG. 4D is a partial perspective view of the foot pedal assembly shown in FIG. 4C, omitting at least the foot pedal assembly base.

One or more raised walls may support an axle 412. For example, two opposing raised walls may include axle mounting holes, with the axle 412 extending therebetween generally along a lateral axis. The axle 412 may be secured in the foot pedal assembly base with fasteners, such as set screws 413 passing through an underside of the foot pedal assembly base 410 (as shown in FIG. 4C) and engaging a hole or flat cutout surface of the axle 412 (as shown in FIG. 4D, with the foot pedal assembly base 410 removed). In other example, the axle 412 may additionally or alternatively be mounted to the foot pedal assembly base with epoxy or other adhesive, interference fit (e.g., press-fit), radial bearings, and/or other suitable manner.

Similar to the axle 212 described above with reference to FIG. 2C, in some variations, the axle 412 may be located at a longitudinally offset position along the foot pedal 420. Accordingly, in variations in which the foot pedal assembly base 410 is similar in length as the foot pedal 420, the axle 412 may be located closer to a rear end of the foot pedal assembly base 410 than a front end of the foot pedal assembly base 410. For example, in one exemplary variation, the foot pedal assembly base may be about 230 mm long in a longitudinal dimension, and the axle may be located about 95 mm from a rear end of the foot pedal assembly base 410 and about 135 mm from a front end of the foot pedal assembly base 410.

In some variations, the foot pedal assembly 400 may include at least one intermediate component 440 placed between the foot pedal assembly base 410 and the foot pedal 420. As shown in FIG. 4B, the intermediate component 440 may be configured to rotate around the axle 412 (e.g., be pivotally coupled to the axle 412), but substantially prevented from moving axially along the axle 412. As described in further detail below, foot pedal 420 (which is pivotally coupled to the axis 420) pivotally moves in tandem with the intermediate component 440 relative to the foot pedal assembly base 410, but moves axially relative to the intermediate component 440. As described in further detail below, the separate relative axial motion of the intermediate component 440 and the foot pedal 420 enables the intermediate component 440 to isolate the mechanics of the foot pedal in its pivoting movement from the mechanics of the foot pedal in its axial movement (e.g., helps prevent axial movement of the foot pedal along the axle from interfering with pivoting movement of the foot pedal).

As shown in FIG. 4B, the intermediate component 440 may include a frame, plate, or other suitable structure interspersed between the foot pedal assembly base 410 and the foot pedal 420. The intermediate component 440 may include at least one opening or other clearance proximate the axle 412 to permit the foot pedal 420 to axially move along axle 412 relative to the intermediate component 440 (e.g., without the intermediate component 440 interfering with the foot pedal's axial movement).

In some variations, the intermediate component 440 may be pivotally coupled to the axle 412. For example, the intermediate component 440 may include laterally opposed holes to align with and receive the axle 412, and one or more bearings (e.g., sleeve bearings) may be disposed in the holes to help facilitate pivotal motion around the axle 412. In some variations, pivoting motion may be supported by the inclusion of lubricious materials in the foot pedal assembly base and/or axle, such as a low friction plastic (e.g., DELRIN).

Pivoting motion of the intermediate component 440 may additionally or alternatively be supported with one or more springs 452 extending between the foot pedal assembly base 410 and the intermediate component 440 providing a spring force. At least one spring 452 may be disposed near a front portion and/or a rear portion of the foot pedal assembly, so as to bias the intermediate component 440 and foot pedal 420 towards a particular pivoted position (e.g., a "neutral" position). For example, as shown in FIG. 4B, the foot pedal assembly base 410 may include at least one spring holder 418 (e.g., peg or pin, recess, or other structure) that is configured to hold in place one end of a spring 452. Similarly, as shown in FIG. 4D, the intermediate component 440 may include at least one spring holder 442 aligned with the spring holder 418 and configured to hold in place an opposite end of spring 452. In some variations, multiple spring holders 442 for each corner of the intermediate component 440 may be provided, for example, to enable tuning of the resilient spring force (e.g., to adjust user feel and the torque required to overcome the spring force) by repositioning the one or more springs 452 relative to the axle, and/or increasing the number of springs 452 generally at each corner. Furthermore, the spring holders 442 and springs 452 may be arranged to bias the intermediate component 440 and the foot pedal 420 toward any suitable pivoted position, such as a forward position, a rearward position, or a central position between the forward and rearward positions, or any suitable angled position. For example, the foot pedal 420 may be biased toward different "neutral" pivoted positions for providing a comfortable angle for the user's foot to rest, depending on, for example, the user's body and/or leg position relative to the foot pedal assembly (e.g., if the user is in an upright seated position, a reclined position, an upright near-standing position, etc.).

When a user applies a pivoting force to the foot pedal 420 that overcomes the spring force provided by the one or more springs 452, the foot pedal 420 and the intermediate component 440 may pivot in tandem forward or rearward around the axle 412. When the user stops applying such a pivoting force, the spring force restores the foot pedal 420 and the intermediate component 440 back to a neutral position. When the user applies a lateral force to move the foot pedal 420, the foot pedal 420 may move axially along the axle 412 while the intermediate component 440 remains substantially in the same axial position. Accordingly, the intermediate component 440 may help isolate the mechanics of the foot pedal in its pivoting movement from the mechanics of the foot pedal in its axial movement, in that the one or more springs 452 supporting pivoting movement are not bent, twisted, or otherwise affected when the foot pedal 420 moves axially independently of the intermediate component 440.

The foot pedal 420 may be slidably and pivotably coupled to the axle 412. As shown in FIG. 4A, the foot pedal 420 may include a platform surface for receiving a user's foot. Furthermore, as shown in FIG. 4A, the foot pedal 420 may include (or be coupled to) a housing, such that the foot pedal 420 and the foot pedal assembly base 410 cooperatively substantially house or enclose other components of the foot pedal assembly 400 described herein (e.g., sensors, axle 412, etc.).

The foot pedal 420 may include one or more features for engaging and interacting with the user's foot. For example, the foot pedal 420 may include an arch bump 422 (e.g., similar to arch bump 222 described above with reference to FIG. 2C) that may engage with the bottom of a user's foot and provide a positional reference for the user's foot. Additionally or alternatively, the foot pedal 420 may include any other suitable positional reference for positioning the user's foot on the foot pedal 420 relative to the axle. As another example, the foot pedal 420 may include one or more side projections 424 (e.g., walls) that the user's foot may push against in order to actuate the foot pedal 420 axially along the axle 412. The side projections 424 may also provide tactile feedback against a side of the user's foot in order to inform the user where on the foot pedal the user's foot is placed (e.g., on a left side or a right side of the foot pedal 420). Furthermore, in some variations, the foot pedal 420 may include one or more sensors (e.g., contact sensors, proximity sensors) configured to detect generally where the user's foot is on the pedal, such that a processor/controller may utilize the sensor signals to display to the user (e.g., on a user screen) a graphical representation of the user's foot on the pedal. Such graphical representations may, for example, improve or confirm a user's awareness of where the user's foot is relative to the pedal.

As shown in FIG. 4D, the foot pedal 420 may include at least one fin 426 or other suitable projection that axially and pivotably couples the foot pedal 420 to the axle 412. For example, the fin 426 may include a hole that is aligned with and receives the axle 423. One or more bearings (e.g., sleeve bearings) may be disposed in the hole to enable axial motion along the axle 412 and pivoting motion around the axle 412. Additionally or alternatively, the fin 426 may include a low-friction or lubricious material (e.g., DELRIN) to help facilitate the movement of the fin 426 along and around the axle.

Similar to the foot pedal 220 described above, the foot pedal 420 may have a first pivoted position (e.g., forward) and a second pivoted position (e.g., rearward) relative to the axle 412. The first and/or second pivoted positions may be "active." The pivoting motion of the foot pedal 420 (as well as the intermediate component 440) may be supported by one or more springs 452 as described above. A switch 434a or other suitable sensor may be configured to detect when the foot pedal 420 is in the first pivoted position. For example, the switch 434a may be disposed between the foot pedal assembly base 410 and a first end of the foot pedal 420 (e.g., coupled to the foot pedal assembly base 410, or coupled to the foot pedal 420) such that when the foot pedal 420 is in the first pivoted position, the switch 434a is engaged or activated, thereby generating a sensor signal indicating that the foot pedal is in the first pivoted position. Similarly, a switch 434b or other suitable sensor may be disposed between the foot pedal assembly base 410 and a second end of the foot pedal 420, such that when the foot pedal 420 is in the second pivoted position, the switch 434b is engaged or activated, thereby generating a sensor signal indicating that the foot pedal is in the second pivoted position. Other suitable sensors, such as those described above with respect to FIGS. 2A-2C, may additionally or alternatively be included in the foot pedal assembly to detect the pivoted position of the foot pedal 420.

Additionally, in some variations, the foot pedal assembly may include at least one spring plunger or other spring-loaded device that further supports at least the foot pedal 420 in its pivoting motion and/or provides feedback to the user about the present pivoted position of the foot pedal 420. The spring plunger may be, for example, a ball-nose spring plunger (e.g., a circumferentially surrounded spring with a bearing ball surface disposed at a distal end of the spring) coupled to the foot pedal assembly base 410 and configured to selectively engage with the foot pedal at or near certain pivoted positions. For example, as shown in FIG. 4B, a spring plunger 450a may be disposed at a front portion of the foot pedal assembly base (from the perspective of a user operating the foot pedal) such that the spring plunger's bearing ball surface is configured to engage a detent on the foot pedal 420 just before the foot pedal reaches its forward pivoted position. When the user pivotally moves the foot pedal toward the forward pivoted position, the user may receive tactile and/or audible feedback (e.g., a soft stop and/or click) resulting from the detent on the foot pedal 420 engaging the upwardly urged spring plunger 450. If the user pivotally moves the foot pedal further, the foot pedal 420 compresses the engaged spring plunger 450 and engages switch 434a, thereby indicating that the foot pedal 420 is in the "active" forward pivoted position. In such a manner, the tactile and/or audible feedback from the spring plunger 450 may indicate to the user that the foot pedal 420 is currently in a neutral pivoted position and/or is nearly actuated to the "active" forward pivoted position, which may, for example, give the user a chance to double-check his or her intention to actuate the pedal to the forward pivoted position. Similarly, another spring plunger 450b may additionally or alternatively be disposed at a rear portion of the foot pedal assembly base such that the spring plunger's bearing ball surface is configured to engage a detent on the foot pedal 420 just before the foot pedal reaches its rearward pivoted position and engages switch 434b, so as to provide the user with feedback regarding the proximity of the foot pedal to the "active" rearward pivoted position. Furthermore, in some variations, the foot pedal assembly may include one or more spring plungers that support sliding motion of the foot pedal 420 and/or provide feedback to the user about the present axial position of the foot pedal in a similar manner as spring plungers 450a and 450b.

Figure 4E:
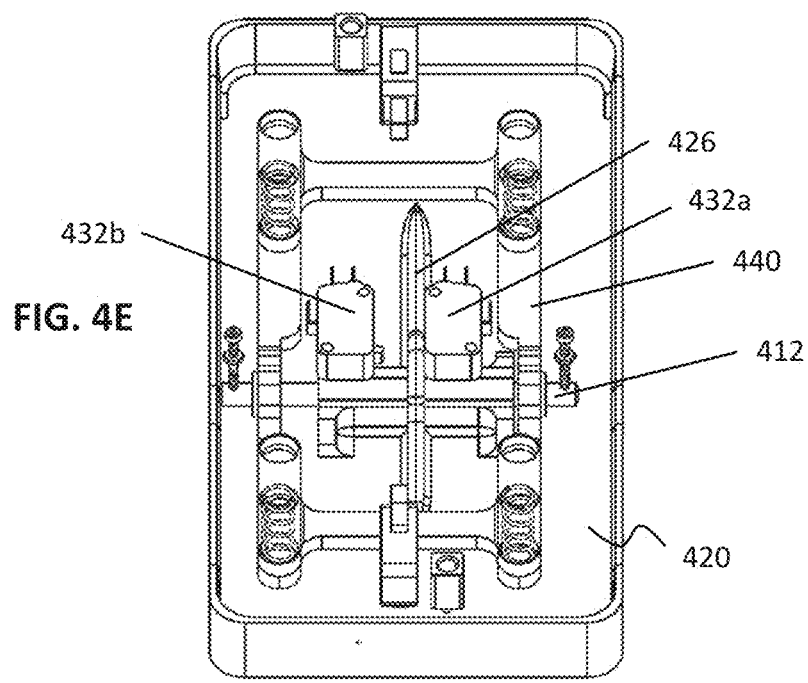
FIGS. 4E and 4F are partial bottom views of the foot pedal assembly shown in FIG. 4D with the foot pedal in a first axial position and the foot pedal in a second axial position, respectively.
Figure 4F:
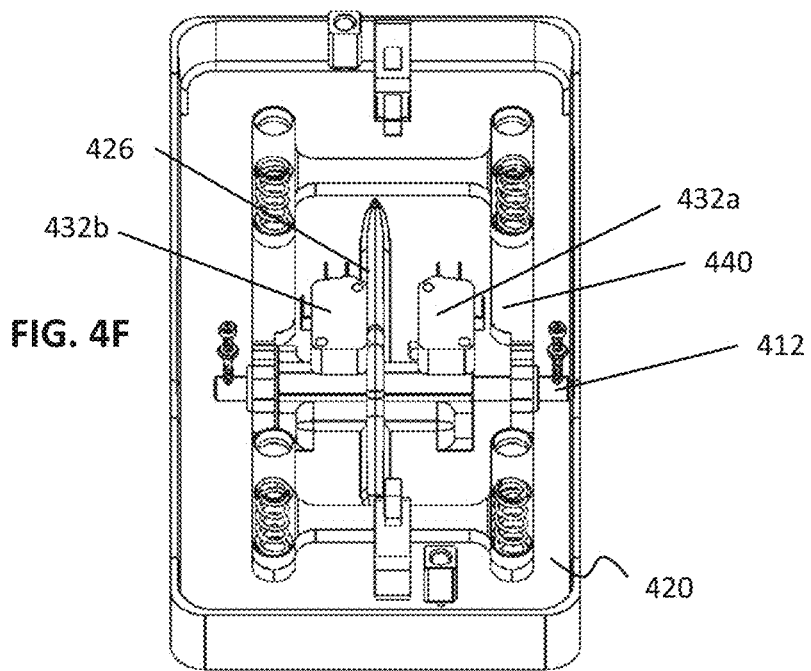

Furthermore, the foot pedal 420 may have a first axial position and a second axial position along the axle 412 (e.g., left-side position and right-side position, from the perspective of a user operating the foot pedal). The first and/or second axial positions may be "active." Lateral switches or other suitable sensors may be used to indicate when the foot pedal 420 is in an "active" axial position when at least a portion of the foot pedal 420 engages a lateral switch. For example, as shown in the underside views depicted in FIGS. 4E and 4F, the fin 426 of the foot pedal 420 may slide axially along the axle 412. As shown in FIG. 4E, when the user axially moves the foot pedal toward a left axial position, the fin 426 may slide along the axle 412 until it engages lateral switch 432a, thereby indicating the foot pedal 420 is in an "active" left-side position. Similarly, as shown in FIG. 4F, when the user axially moves the foot pedal toward a right axial position, the fin 426 may slide along the axle 412 until it engages lateral switch 432b, thereby indicating the foot pedal 420 is in an "active" right-side position. As shown in FIGS. 4E and 4F, the intermediate component 440 may include an opening or other suitable clearance to enable the fin 426 to move along the axle 412 while still engaged with the axle 412.

In some variations, the foot pedal assembly may include one or more elements that modulate the force (e.g., from the user's foot) required to maintain the foot pedal 420 at various axial locations within its axial range of motion, such that the foot pedal 420 tends to be stable in one or more selected axial locations. Different user experiences with the foot pedal assembly may depend on the force profile (examples described below) provided by force-modulating elements over various axial positions of the foot pedal along the axle 412.

Figure 5A:
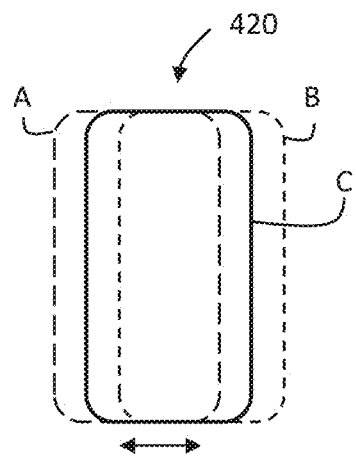
FIG. 5A is a schematic illustration of a foot pedal having three translated positions.
Figure 5B:
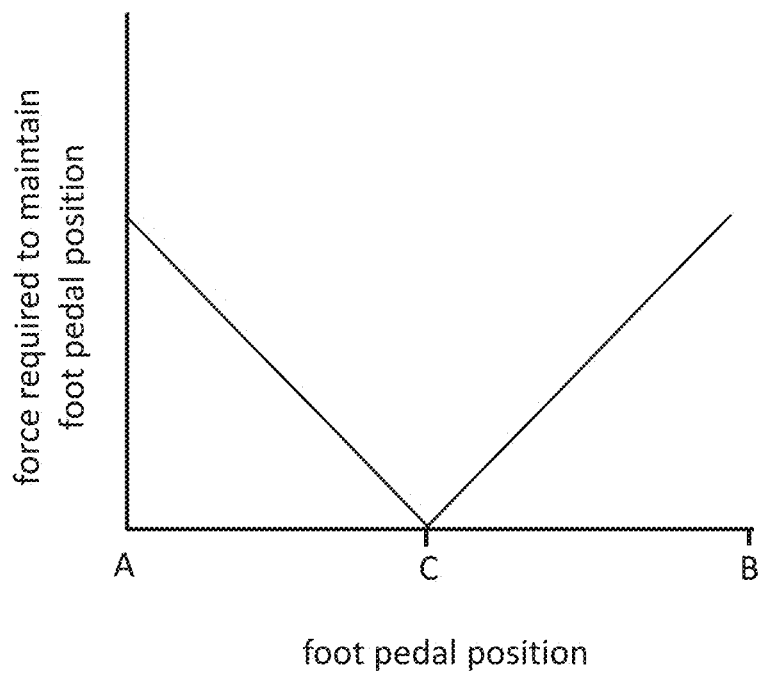
FIG. 5B is a schematic illustration of how a foot pedal is biased toward one stable translated position.

In one variation, the foot pedal 420 may have one stable axial position (e.g., a "neutral" position). For example, as shown in FIG. 5A, a foot pedal 420 may be movable between two axial positions A and B, as well as an axial position C between axial positions A and B. The foot pedal assembly may, in some variations, include one or more compression springs coupled between a left-side portion of the intermediate component 440 and a left-side portion of the foot pedal 420, such that the compression spring urges the foot pedal 420 toward the axial position C from the left side of the foot pedal assembly. Similarly, one or more compression springs may be coupled between a right-side portion of the intermediate component 440 and a right-side portion of the foot pedal 420, such that the compression spring urges the foot pedal 420 toward the axial position C from the right side of the foot pedal assembly. Additionally or alternatively, one or more compression springs may be coupled between the base 410 and the foot pedal 420 to urge the foot pedal 420 toward the neutral axial position (e.g., in variations lacking an intermediate component 440). Accordingly, as shown in the exemplary force profile shown in FIG. 5B, the user may apply an axial force to actuate the foot pedal toward axial positions A or B, and the foot pedal may be restored to the axial position C when the user ceases applying the axial force. As such, for example, positions A and B may be "active" and correlated to instruments or other functionalities that are selected only in the presence of the user actuating the foot pedal to an active axial position, while position C may be "neutral" position that is selected by default in the absence of the user's actuation of the foot pedal. In other variations, other kinds of biasing members (e.g., other kinds of springs, etc.) may provide a similar biasing of the foot pedal 420 toward a neutral axial position, and with other suitable force profiles (e.g., a non-linear profile).

Figure 6A:
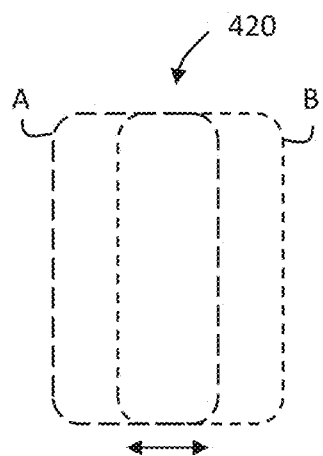
FIG. 6A is a schematic illustration of a foot pedal having two translated positions.
Figure 6B:
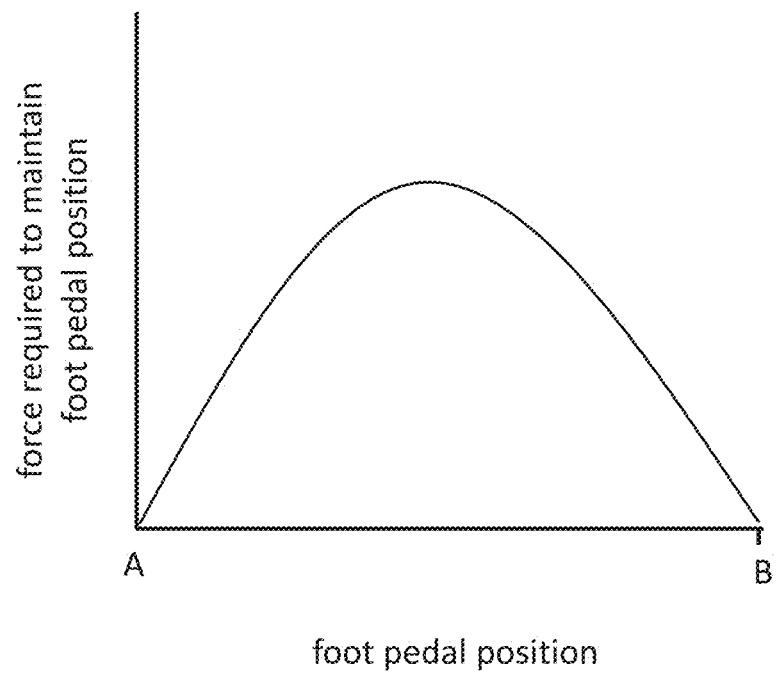
FIG. 6B is a schematic illustration of how a foot pedal is bi-stable between the two translated positions shown in FIG. 6A.

In another variation, the foot pedal 420 may be bi-stable in its axial range of motion along the axle 412, or stable only in either of two axial positions along the axle. As shown in FIG. 6A, a foot pedal 420 may be movable between two axial positions A and B (e.g., opposite ends of an axial range of motion or travel). As shown in FIG. 6B, a bi-stable foot pedal 420 may be stable in either of the axial positions A and B, and tend to move toward the closer of axial position A or B as it moves throughout its axial range of motion. For example, as shown in the exemplary force profile shown in FIG. 6B, the user may not be required to exert force either left or right on the pedal shown in FIG. 6A in order to maintain the foot pedal position at axial position A or B. In other variations, a bi-stable foot pedal may have any other suitable force profile between "active" axial positions (e.g., a profile with linear slopes).

In one variation of a bi-stable foot pedal, the foot pedal assembly may include one or more magnets. For example, the foot pedal assembly 400 shown in FIGS. 4A-4F may include at least a first magnet (or magnetic material) coupled to a left-side portion of the foot pedal 420 and at least a second magnet coupled to a left-side portion of intermediate component 440, where the first and second magnets are arranged proximate to one another (e.g., on interfacing surfaces of the foot pedal 420 and intermediate component 440) such that the they magnetically attract one another, thereby pulling the foot pedal 420 closer to the left portion of the intermediate component 440 and into a left-side axial position. Similarly, the foot pedal assembly 400 may include magnets on right-side portions of interfacing surfaces of the foot pedal 420 and intermediate component 440 such that the magnets attract one another and pull the foot pedal 420 closer to a right portion of the intermediate component 440 and into a right-side axial position. Additionally or alternatively, magnets or magnetic material may be disposed on proximate or interfacing surfaces of the foot pedal assembly base 410 and the foot pedal 420 (e.g., in variations lacking an intermediate component 440). Accordingly, when the user actuates the foot pedal 420 toward the left-side or right-side axial position, a magnetic attractive force provided by the magnets urges the foot pedal 420 to the left-side or right-side axial position. As such, for example, positions A and B may be "active" and correlated to selectable instruments or other functionalities that remain selected until the user affirmatively actuates the foot pedal to move to another axial position. In other variations, a similar bi-stable effect for the foot pedal 420 may be achieved with magnets providing magnetic repulsive force.

Figure 7A:
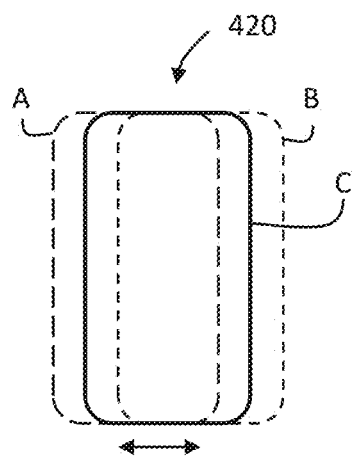
FIG. 7A is a schematic illustration of a foot pedal having three translated positions.
Figure 7B:
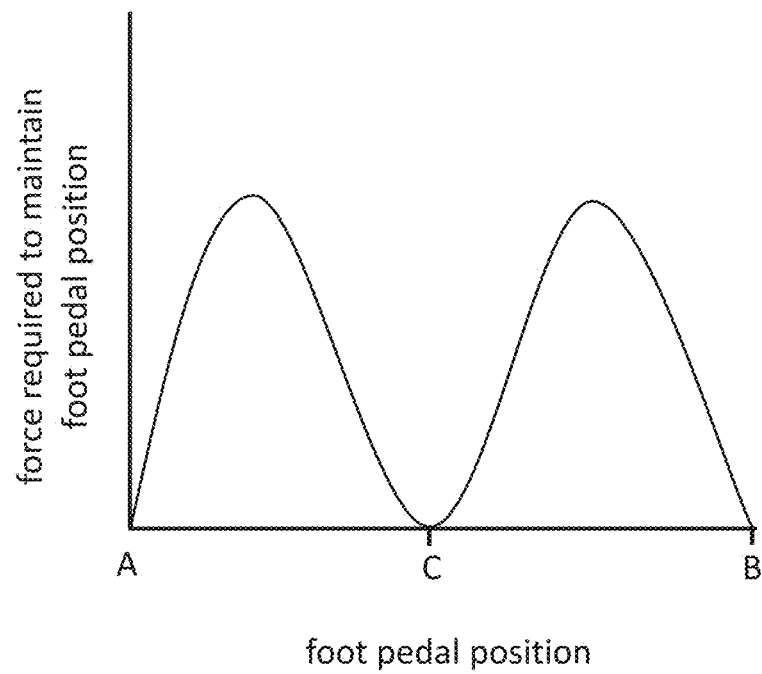
FIG. 7B is a schematic illustration of how a foot pedal is movable between the three stable translated positions shown in FIG. 7A.

In yet another variation, the foot pedal 420 may include at least three stable axial positions. For example, as shown in FIG. 7A, a foot pedal 420 may be movable between two axial positions A and B, as well as an axial position C between axial positions A and B. One or more compression springs (or other biasing members) may be disposed on the left and right sides of the foot pedal assembly (e.g., between the intermediate component and the foot pedal, or between the foot pedal assembly base and the foot pedal) as described above with reference to FIGS. 5A and 5B, which may urge the foot pedal 420 toward the axial position C. Additionally in combination with the one or more compression springs, one or more magnets may be disposed on the left and right sides of the foot pedal assembly (e.g., between the intermediate component and the foot pedal, or between the foot pedal assembly base and the foot pedal) as described above with reference to FIGS. 6A and 6B. Accordingly, as described generally by the force profile depicted in FIG. 7B, when the user actuates the foot pedal 420 toward axial position A or B up to a certain threshold distance away from the axial position C, a spring force provided by the compression springs tends to urge the foot pedal 420 toward the axial position C. When the user actuates the foot pedal 420 toward axial position A or B beyond the threshold distance away from the axial position C, an attractive magnetic force provided by the magnets may overcome the spring force and pull and hold the foot pedal 420 to a stable axial position A or B. The user may furthermore exert a medial force toward axial position C in order to overcome the magnetic force and allow the foot pedal to be restored to the axial position C. Other combinations of elements may be used to provide a force profile generally similar to that shown in FIG. 7B or any other suitable force profile (e.g., one or more polymagnets providing a customized magnetic force profile, one or more electromagnets providing a customized magnetic force profile which may be modulated by an electrical circuit, one or more motors that are controllable (e.g., by the processor/controller 320) to selectively create active resistance to the relative motion between the foot pedal and the foot pedal assembly base, other devices for passive and/or active force feedback, etc.).

In some variations, at least one of the axial positions of the foot pedal 420 (e.g., a "neutral" axial position, such as position C shown in FIG. 5A or 7A) may be correlateable to a lock-out function (e.g., a safety lock-out function). For example, although the foot pedal 420 may be physically capable of pivoting forward or rearward while in a "neutral" axial position, such pivoting may be disconnected from control of any aspect of the robotic system as long as any sensors detect that the foot pedal is in the "neutral" axial position (e.g., sensors affirmatively detecting the neutral axial position, or the absence of detection of any "active" axial positions, etc.). In other words, there may be no action (e.g., no control or actuation of any functionality of the robotic system) in response to a forward or rearward pivoting of the foot pedal 420 while the foot pedal 420 is in the "neutral" axial position. For example, in variations in which "active" axial positions correspond to selected surgical instruments or arms and "active" pivoted positions correspond to functions of the selected surgical instrument or arms, a "neutral" axial position may mean the user has not selected a particular surgical instrument or arm to control, so any pivoting of the foot pedal 420 is moot in terms of controlling a particular robotic function. Such pivoting of the foot pedal 420 while in the neutral axis may, however, be useful to the user in providing feedback on the current axial position of the foot pedal (e.g., for spatial awareness of where the foot pedal is relative to the foot pedal assembly base), providing a safe opportunity for the user to verify that the foot pedal has not mechanically failed in its pivoting range of motion, etc. Alternatively, in some variations, the foot pedal assembly may include a physical stop that substantially physically prevents the foot pedal from pivoting.

In some variations, the foot pedal assembly 400 may include at least one lock for maintaining a particular pivoted position and/or a particular axial position of the foot pedal.

For example, a lock may include one or more electromagnets that pull or repel the portions of the foot pedal closer or farther from the foot pedal assembly base, where the electromagnets may be selectively powered to hold the foot pedal in a selected position or release the foot pedal from the selected position. As another example, a lock may include latches, mechanical interference fits, or any suitable mechanism for selectively holding and releasing the foot pedal relative to a selected position. Such a lock may be useful, for example, to maintain a particular pivoted position and/or particular axial position while the foot pedal assembly is not in use (e.g., in storage), while a user steps away from the user console, etc.

Figure 8A:
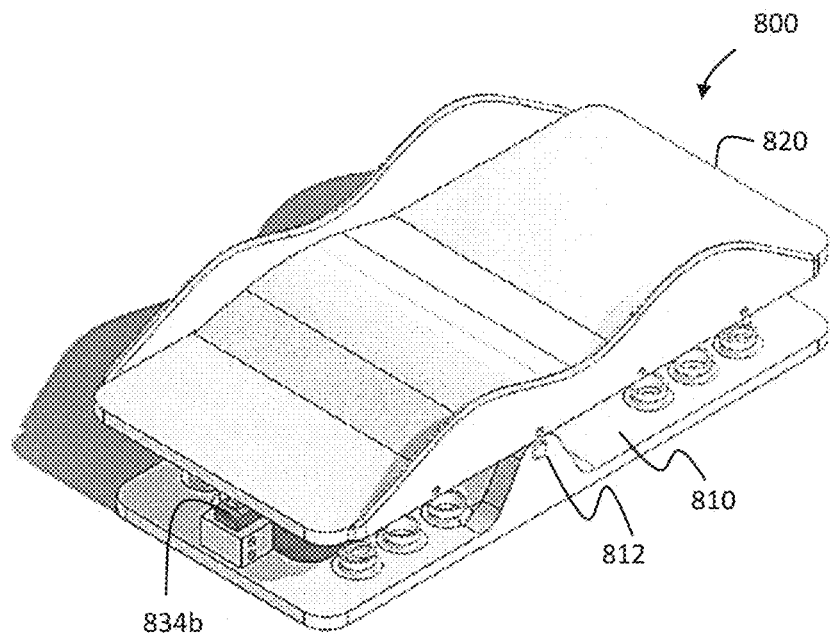
FIGS. 8A-8C are a perspective view, a side view, and an exploded view, respectively, of another variation of a foot pedal assembly.
Figure 8B:
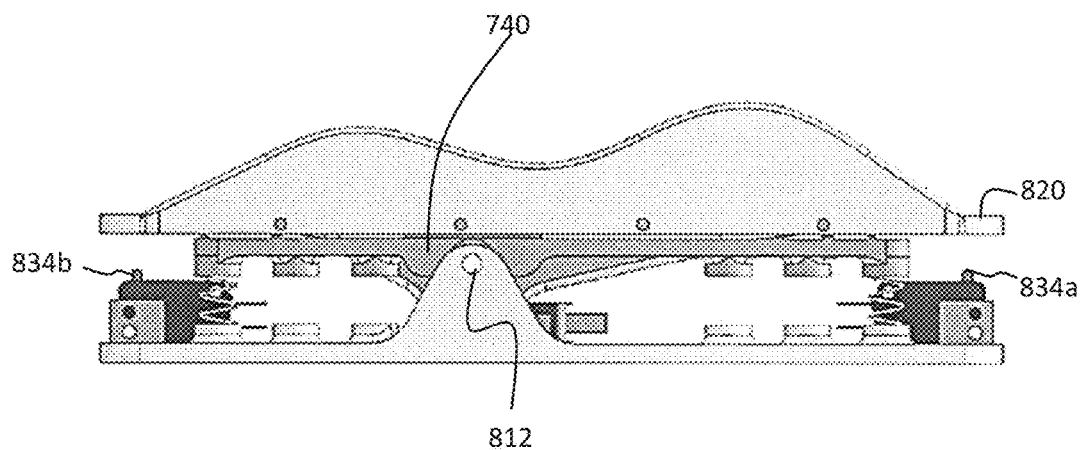
Figure 8C:
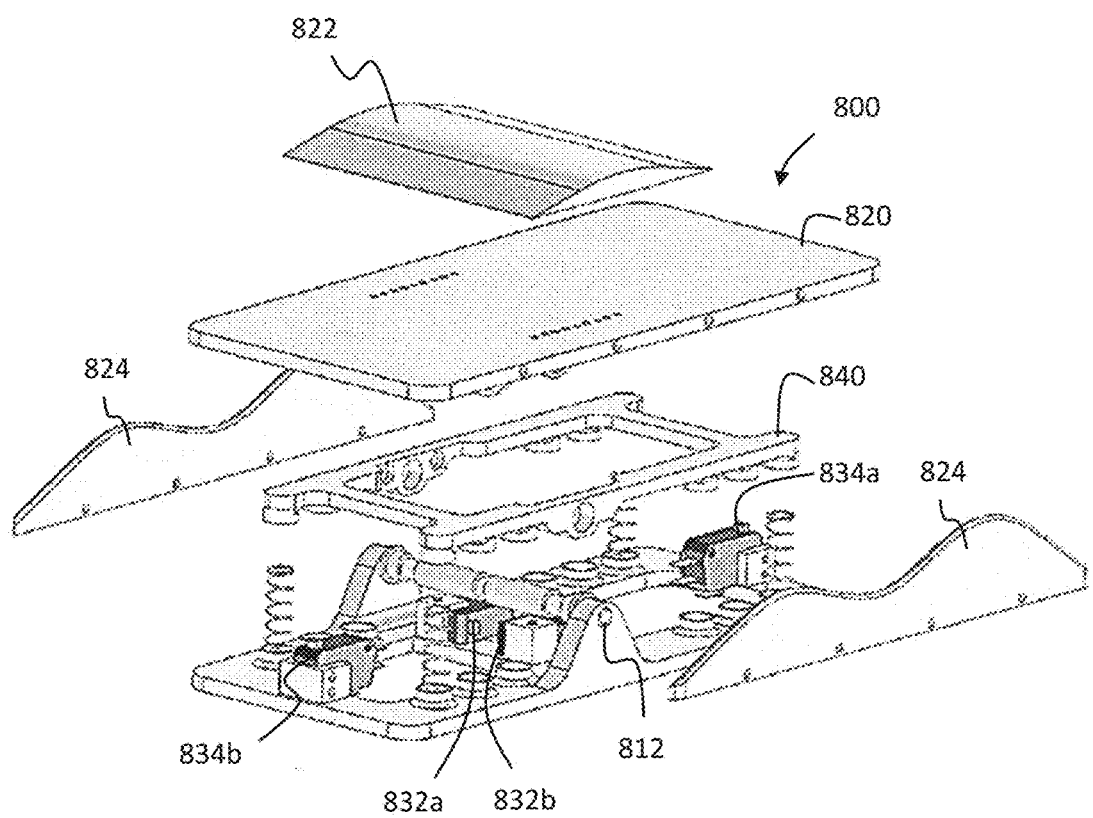

Another exemplary variation of a foot pedal assembly 800 is shown in FIGS. 8A-8C. The foot pedal assembly 800 may be similar to the foot pedal assembly 400 described above with reference to FIGS. 4A-4F, except as described below. For example, like the foot pedal assembly 400, the foot pedal assembly 800 for controlling a robotic surgical system includes a foot pedal assembly base 810 including an axle 812, a foot pedal 820 slidably and pivotally coupled to the axle 812, and a sensor arrangement including one or more sensors configured to detect an axial position of the foot pedal 820 along the axle 812 (e.g., sensors 832a and 832b shown in FIG. 8C) and/or a pivoted position of the foot pedal 820 around the axle 812 (e.g., sensors 834a and 834b shown in FIG. 8B). The foot pedal 820 may include a positional reference 822 (e.g., arch bump) for locating a user's foot relative to the axle 812, and/or sidewalls 824. Furthermore, the foot pedal assembly 800 may include an intermediate component 840 located between the foot pedal assembly base 810 and the foot pedal 820 which may help isolate the mechanics of the foot pedal in its axial movement from the mechanics of the foot pedal in its pivotal movement, similar to intermediate component 440 described above. Furthermore, in some variations, at least the foot pedal assembly base 810, the intermediate component 840, and the foot pedal 820 may be self-contained. In contrast to the foot pedal assembly 400 shown in FIGS. 4A-4F, however, the foot pedal assembly 800 does not substantially enclose components (springs, sensors, etc.) in an enclosed housing. For example, the foot pedal assembly base 810 may include an open platform with axle supports supporting the axle 812.

Figure 9A:
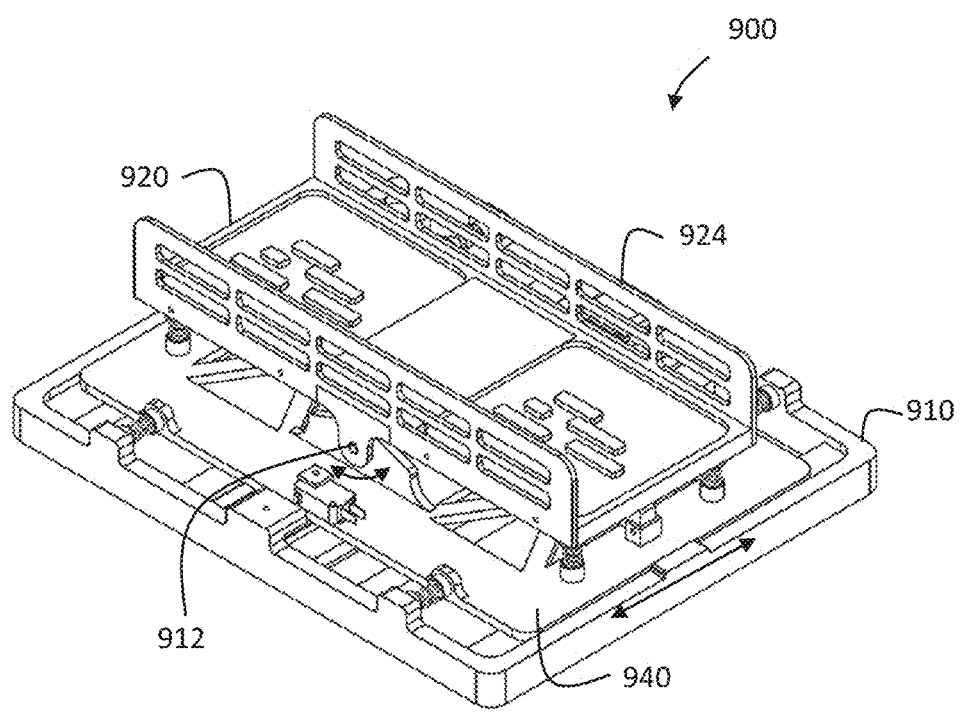
FIG. 9A is a perspective view of another variation of a foot pedal assembly.

Another exemplary variation of a foot pedal assembly 900 shown in FIGS. 9A-9C, which may be similar to the foot pedal assembly 400 described above with reference to FIGS. 4A-4F, except as described below. The foot pedal assembly 900 for controlling a robotic surgical system includes a foot pedal assembly base 910, an intermediate component 940 slidingly engaged with the foot pedal assembly base 910 and supporting an axle 912, and a foot pedal 920 pivotally coupled to the axle 912. In this variation, the motion of the intermediate component 940 relative to the foot pedal assembly base 910 provides the translational range of motion of the foot pedal 920 (which is coupled to the intermediate component 940) relative to the foot pedal assembly base 910. In other words, the translational range of motion of the foot pedal 920 is functionally decoupled from the axle 912. Additionally, a sensor arrangement including one or more sensors may be configured to detect a translated position and/or a pivoted position of the foot pedal 920 relative to the foot pedal assembly base 910.

Figure 9B:
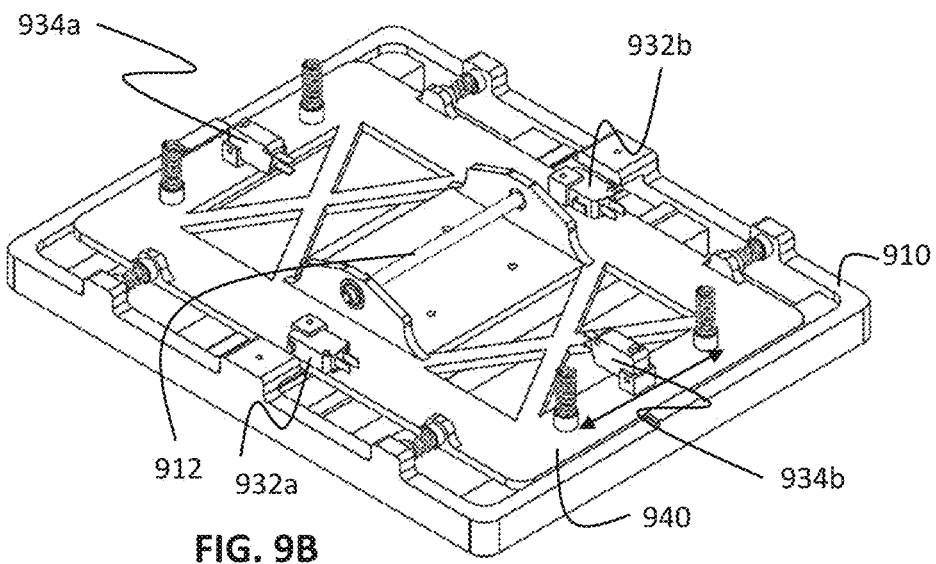
FIG. 9B is a partial perspective view of the variation of a foot pedal assembly shown in FIG. 9A, omitting at least the foot pedal.
Figure 9C:
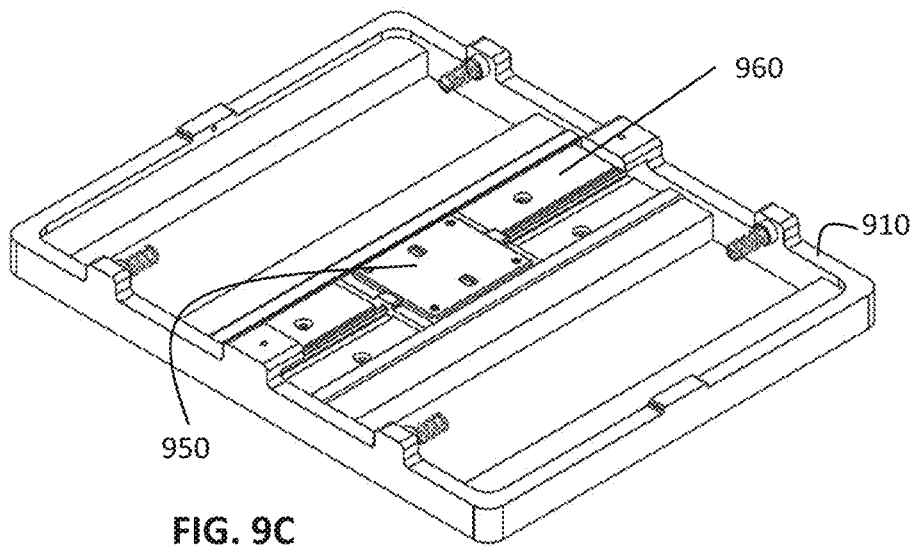
FIG. 9C is a partial perspective view of the variation of a foot pedal assembly shown in FIG. 9A, omitting at least the foot pedal and the intermediate component.

As shown in FIG. 9C, the foot pedal assembly base 910 may include a carriage 950 traveling on at least one track 960. The intermediate component 940 may be coupled to the carriage 950, such that the intermediate component 940 may travel relative to the foot pedal assembly base along the at least one track 960. As shown in FIG. 9C, the foot pedal assembly base 910 may include, for example, one track substantially parallel to the axle 912, thereby allowing the intermediate component 940 and the foot pedal 920 to travel in tandem in a axial direction. The sensor arrangement may include, for example, sensors 932a and 932b (e.g., coupled to the intermediate component 940 as shown in FIG. 9B) configured to detect translated positions of the intermediate component 940 and the foot pedal 920. In other arrangements, the foot pedal assembly base 910 may include one or more tracks oriented along any suitable direction, so as to allow the intermediate component 940 and foot pedal 920 to additionally or alternatively travel in directions other than an axial direction aligned with axle 912. For example, one or more tracks may be orthogonal to the axle 912 (e.g., oriented to permit forward and/or backward translation, if the axle 912 is directed left and right relative to the user's foot), or any other angle relative to the axle 912. Furthermore, the track 960 may be nonlinear (e.g., circular, elliptical, curvilinear, etc.) to permit travel of the intermediate component 940 and foot pedal 920 in other suitable directions. In yet other variations, the intermediate component 940 and foot pedal 920 may travel freely (i.e., without the constraint of a track 960) in translation or other suitable manner along the foot pedal assembly base. The sensor arrangement may accordingly include sensors (e.g., switches, capacitive sensors, etc.) along the track, at the endpoints of the track, etc. to detect the translated position of the intermediate component 940 and foot pedal 920 relative to the foot pedal assembly base 910.

As shown in FIG. 9B, the intermediate component 940 may include one or more axle supports to support an axle 912. A shown in FIG. 9A, the foot pedal 920 may be pivotally coupled to the axle 912, such that the foot pedal 920 may pivot relative to the intermediate component 940, (and relative to the foot pedal assembly base 910 since intermediate component 940 is coupled to the foot pedal assembly base 910). Similar to variations described above, the axle 912 may be placed in an offset location (e.g., slightly rearward of a centerline of the foot pedal 920). The sensor arrangement may include, for example, sensors 934a and 934b (e.g., coupled to the intermediate component 940 as shown in FIG. 9B, or coupled to the foot pedal 940, etc.) configured to detect the pivoted position of the foot pedal 940. Furthermore, the foot pedal may include sidewalls 924 to help locate the user's foot relative to the axle 912 and/or provide the user with spatial awareness of his or her foot's location on the foot pedal 920.

The various components of the foot pedal assembly (e.g., foot pedal assembly base, foot pedal, intermediate component, etc.) may include a rigid or semi-rigid material such as a suitable plastic or metal. For example, some or all of the components of the foot pedal assembly may include a rigid or semi-rigid plastic (e.g., polycarbonate, acrylonitrile butadiene styrene (ABS), nylon, etc.), though some components may include metal (e.g., aluminum, stainless steel, bronze, etc.). For example, the foot pedal assembly base, foot pedal, and/or intermediate component may primarily include plastic, while the axle to which the foot pedal is coupled may primarily include metal. At least some of the foot pedal assembly base, foot pedal, and/or intermediate component may, for example, be injection molded, 3D printed, casted, milled, or made in any suitable manner. In some variations, the foot pedal assembly base, foot pedal, and/or intermediate component may be integrally formed, while in other variations, at least some portions of these components may be separately formed and coupled via fasteners, ultrasonic welding, mechanical interlocking parts, etc.

Method for Controlling a Robotic Surgical System

Figure 10:
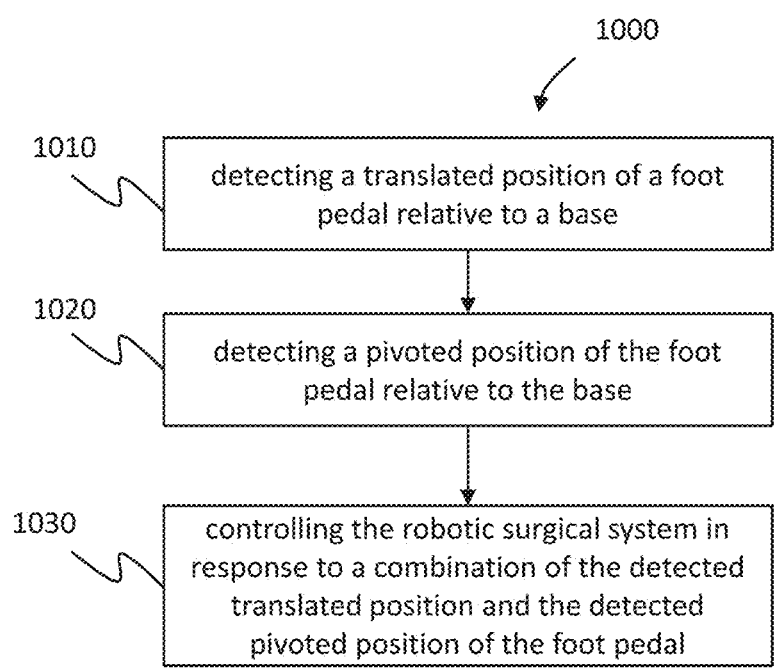
FIG. 10 is a flowchart illustrating one method for controlling a robotic surgical system using a multi-functional foot pedal assembly.

Generally, as shown in FIG. 10, a method 1000 for controlling a robotic surgical system includes detecting a translated position of a foot pedal relative to a foot pedal assembly base 1010, detecting a pivoted position of the foot pedal relative to the foot pedal assembly base 1020, and controlling the robotic surgical system in response to a combination of the detected translated position and the detected pivoted position of the foot pedal 1030. The method 1000 may be used in combination with, for example, any suitable one or more variations of the foot pedal assembly described herein, or any other suitable foot pedal system.

In some variations, different combinations of different translated positions and pivoted positions that are detected may be correlateable to different functions of the robotic surgical system. For example, in one variation, different translated positions of the foot pedal may generally correspond to control of different surgical instruments (e.g., instruments on different robotic arms), such that a user may, for example, move the foot pedal to a selected translated position to enable control of a selected surgical instrument. While the foot pedal is in the selected translated position, different pivoted positions of the foot pedal may generally correspond to actuation of different functions of the selected surgical instrument (e.g., a primary active function or a secondary active function of the surgical instrument). In other variations, different translated positions of the foot pedal need not correspond to different surgical instruments or robotic arms. As such, various combinations of translated positions and pivoted positions of the foot pedal may correspond to any suitable assortment of distinct functions of the robotic surgical system (e.g., an instrument clutch mode, camera control, selection or designation of a "left hand" and "right hand" pair or other suitable subset of available robotic arms/instruments for control, etc.).

For example, in some variations, the method may be used in combination with a system including a foot pedal assembly having a foot pedal that is translatable between two translated positions (e.g., a first or left-side axial position and a second or right-side axial position) and/or pivotable between two pivoted positions (e.g., a forward pivoted position and a rearward pivoted position). Some of these positions may be "active." If the detected translated position of the foot pedal is a first "active" translated position, subsequent pivoting actuation of the foot pedal may be correlated to functionality of a first surgical instrument. For example, while the foot pedal is determined to be in the first translated position, controlling the robotic surgical system 1030 may include controlling a first function of the first instrument in response to detecting that the foot pedal is in a first "active" pivoted position, and controlling a second function of the first instrument in response to detecting that the foot pedal is in a second "active" pivoted position. Similarly, if the detected translated position of the foot pedal is a second "active" translated position, subsequent pivoting actuation of the foot pedal may be correlated to functionality of a second surgical instrument. For example, while the foot pedal is determined to be in the second translated position, controlling the robotic surgical system 1030 may include controlling a first function of the second instrument in response to detecting that the foot pedal is in a second "active" pivoted position, and controlling a second function of the second instrument in response to detecting that the foot pedal is in a second "active" pivoted position.

Furthermore, in some variations, the method may be used in combination with a system including a foot pedal assembly having a foot pedal that is further translatable to a "neutral" translated position, such as between the first and second translated positions. In such variations, if the detected translated position of the foot pedal is a "neutral" translated position, controlling the robotic surgical system 1030 may, for example, include inhibiting control of one or more functions of a surgical instrument (e.g., if the user pivots the foot pedal while the foot pedal is in a neutral translated position, then there may be no control signal generated to control a particular function of a particular surgical instrument).

In one exemplary variation, the method may be used in combination with a system including two of the above-described foot pedal assemblies, each foot pedal assembly having a foot pedal with at least two "active" translated positions and at least two "active" pivoted positions. One foot pedal assembly may be designated as a left foot pedal assembly for being controlled by a user's left foot, and the other foot pedal assembly may be designated as a right foot pedal assembly for being controlled by a user's right foot. In this variation, controlling the robotic surgical system 1030 may include controlling the robotic surgical system based on the detected translated and pivoted positions of the left foot pedal (the foot pedal in the left foot pedal assembly). For example, the method may include rotating through selection of desired "left hand" and "right hand" instruments in response to detecting that the left foot pedal is in a left-side axial position and a forward and/or rearward pivoted position (e.g., forward or rearward pivoting may "scroll" through a displayed graphical representation of a set of instruments available for selection as "left hand" and "right hand" instruments, scroll through different possible paired combinations of available instruments, etc.). As another example, the method may include engaging an instrument clutch mode (e.g., in which movement of handheld user interface devices does not move surgical instruments otherwise controlled by the user interface devices) in response to detecting that the left foot pedal is in a right-side axial position and a forward pivoted position. As another example, the method may include controlling a camera (e.g., increasing a zoom view) in response to detecting that the left foot pedal is in a right-side axial position and a rearward pivoted position.

Furthermore, in this variation, controlling the robotic surgical system 1030 may include controlling the robotic surgical system based on the detected translated and pivoted positions of the right foot pedal (the foot pedal in the right foot pedal assembly). For example, the method may include actuating a first function of a "left hand" instrument in response to detecting that the foot pedal is in a left-side axial position and a forward pivoted position, and actuating a second function of a "left hand" instrument in response to detecting that the foot pedal is in a left-side axial position and a rearward pivoted position. As another example, the method may include actuating a first function of a "right hand" instrument in response to detecting that the foot pedal is in a right-side axial position and a forward pivoted position, and actuating a second function of a "right hand" instrument in response to detecting that the foot pedal is in a right-side axial position and a rearward pivoted position. The functions of an instrument may, for example, include firing an energy pulse of a certain energy level, actuating graspers, actuating cutters, etc., or any other suitable function of a surgical instrument.

In another exemplary variation, the method may be used in combination with a system including three of the above-described foot pedal assemblies, each foot pedal assembly having a foot pedal with at least two "active" translated positions and at least two "active" pivoted positions. A first foot pedal assembly may be designated as a left foot pedal assembly for being controlled by a user's left foot, a second foot pedal assembly may be designed as a right foot pedal assembly for being controlled by a user's right foot, and a third foot pedal assembly (e.g., located between the first and second foot pedal assemblies) may be designated as a central foot pedal assembly for being controlled by either the user's left foot or the user's right foot. The first and second foot pedal assemblies may be operated in a manner similar to the left foot pedal assembly and the right foot pedal assembly, respectively, as described above. For example, the method may include rotating through selection of desired controllable instruments, engaging an instrument clutch mode and/or controlling a camera in response to detecting various positions of the left foot pedal assembly. The method may include actuating functions of first and second selected instruments (e.g., attached to first and second robotic arms) in response to detecting various positions of the right foot pedal assembly. Furthermore, in this variation with three foot pedal assemblies, the method may include actuating functions of third and/or fourth selected instruments (e.g., attached to third and fourth robotic arms) in response to detecting various positions of the central foot pedal assembly. Accordingly, the three pedals may enable control of up to, for example, twelve different functionalities of the robotic surgical system.

Other aspects of the method may include controlling other suitable functions of the different surgical instruments and/or other portions of the robotic surgical system, as described elsewhere herein.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A foot pedal assembly for controlling a robotic surgical system, comprising:
   a foot pedal assembly base comprising an axle;
   a foot pedal slidably and pivotally coupled to the axle; and
   a sensor arrangement configured to detect an axial position of the foot pedal along the axle and a pivoted position of the foot pedal around the axle,
   wherein different combinations of different detected axial positions and detected pivoted positions are correlateable to different functions of the robotic surgical system.

2. The foot pedal assembly of claim 1, wherein the axle is a horizontal axle, and the foot pedal assembly is self-contained.

3. The foot pedal assembly of claim 1, wherein the detected axial position is correlateable to control of a user-selected instrument.

4. The foot pedal assembly of claim 3, wherein the detected pivoted position is correlateable to control of a function of the user-selected instrument.

5. The foot pedal assembly of claim 4, wherein the foot pedal is slidable between a first axial position and a second axial position, and pivotable between a first pivoted position and a second pivoted position.

6. The foot pedal assembly of claim 5, wherein the foot pedal is bi-stable between the first and second axial positions.

7. The foot pedal assembly of claim 5, wherein the foot pedal further comprises a third axial position between the first and second axial positions, wherein the third axial position corresponds to a safety lock-out function of the robotic surgical system.

8. The foot pedal assembly of claim 7, further comprising at least one biasing element urging the foot pedal to the third axial position.

9. The foot pedal assembly of claim 5, further comprising at least one biasing element urging the foot pedal to a third pivoted position between the first and second pivoted positions.

10. The foot pedal assembly of claim 1, further comprising an intermediate component interspersed between the foot pedal assembly base and foot pedal.

11. The foot pedal assembly of claim 10, wherein the intermediate component is pivotally coupled to the axle.

12. The foot pedal assembly of claim 10, wherein the foot pedal is laterally movable relative to the intermediate component.

13. The foot pedal assembly of claim 1, wherein the foot pedal is pivotally coupled to the axle at a location farther from a first foot pedal end than a second foot pedal end opposite the first pedal end.

14. The foot pedal assembly of claim 1, wherein the sensor arrangements comprises one or more switches.

15. The foot pedal assembly of claim 1, wherein the foot pedal is coupled to the axle such that the axle is farther from a first foot pedal end than from a second foot pedal end opposite the first foot pedal end.

16. The foot pedal assembly of claim 15, wherein the foot pedal comprises a positional reference located farther from the first pedal end than from the second pedal end.

17. The foot pedal assembly of claim 1, further comprising a second foot pedal assembly base comprising a second axle, and a second foot pedal pivotally coupled to a second axle.

18. A method for controlling a robotic surgical system, the method comprising:
   detecting a translated position of a foot pedal along a horizontal axle coupled to a foot pedal assembly base, wherein the foot pedal and the foot pedal assembly base are in a self-contained foot pedal assembly;
   detecting a pivoted position of the foot pedal relative to the foot pedal assembly base; and
   controlling the robotic surgical system in response to a combination of the detected translated position and the detected pivoted position of the foot pedal.

19. The method of claim 18, wherein different combinations of different detected translated positions and detected pivoted positions are correlateable to control of different functions of the robotic surgical system.

20. The method of claim 18, wherein the foot pedal is translatable between a first translated position and a second translated position, and pivotable between a first pivoted position and a second pivoted position.

21. The method of claim 20, wherein when the detected translated position is the first translated position, controlling the robotic surgical system comprises controlling a first function of a first surgical instrument if the detected pivoted position is the first pivoted position, and controlling a second function of the first surgical instrument if the detected pivoted position is the second pivoted position.

22. The method of claim 20, wherein when the detected translated position is the second translated position, controlling the robotic surgical system comprises controlling a first function of a second surgical instrument if the detected pivoted position is the first pivoted position, and controlling a second function of the second surgical instrument if the detected pivoted position is the second pivoted position.

23. The method of claim 20, wherein the foot pedal is further translatable to a third translated position between the first and second translated positions.

24. The method of claim 23, wherein when the detected translated position is the third translated position, controlling the robotic surgical system comprises inhibiting control of one or more functions of a surgical instrument.

25. The method of claim 18, wherein controlling the robotic surgical system comprises controlling an instrument clutch mode in response to the combination of the detected translated position and the detected pivoted position of the foot pedal.

26. The method of claim 18, wherein controlling the robotic surgical system comprises designating one or more surgical instruments for control in response to a combination of the detected translated position and the detected pivoted position of the foot pedal.

* * * * *